(12) United States Patent
Nelson et al.

(10) Patent No.: US 11,069,054 B2
(45) Date of Patent: Jul. 20, 2021

(54) SYSTEM AND METHOD FOR AUTOMATED DETECTION AND MONITORING OF DYSPLASIA AND ADMINISTRATION OF IMMUNOTHERAPY AND CHEMOTHERAPY

(71) Applicant: VISIONGATE, INC., Phoenix, AZ (US)

(72) Inventors: Alan C. Nelson, Phoenix, AZ (US); Michael G. Meyer, Phoenix, AZ (US); Daniel J. Sussman, Tempe, AZ (US)

(73) Assignee: VisionGate, Inc., Phoenix, AZ (US)

( * ) Notice: Subject to any disclaimer, the term of this patent is extended or adjusted under 35 U.S.C. 154(b) by 396 days.

(21) Appl. No.: 15/403,940

(22) Filed: Jan. 11, 2017

(65) Prior Publication Data

US 2017/0140533 A1    May 18, 2017

Related U.S. Application Data

(63) Continuation-in-part of application No. PCT/US2016/068859, filed on Dec. 28, 2016.

(60) Provisional application No. 62/367,000, filed on Jul. 26, 2016, provisional application No. 62/273,127, filed on Dec. 30, 2015.

(51) Int. Cl.

| A61K 31/167 | (2006.01) |
| G06T 7/00 | (2017.01) |
| G01N 33/483 | (2006.01) |
| A61K 31/5578 | (2006.01) |
| A61K 31/593 | (2006.01) |
| G01N 15/14 | (2006.01) |
| G06K 9/00 | (2006.01) |
| G01N 15/10 | (2006.01) |

(52) U.S. Cl.
CPC .......... *G06T 7/0012* (2013.01); *A61K 31/167* (2013.01); *A61K 31/5578* (2013.01); *A61K 31/593* (2013.01); *G01N 15/14* (2013.01); *G01N 15/1434* (2013.01); *G01N 15/1468* (2013.01); *G01N 33/4833* (2013.01); *G06K 9/00147* (2013.01); *G06K 9/00201* (2013.01); *G01N 2015/1006* (2013.01); *G01N 2015/1445* (2013.01); *G06T 2207/10101* (2013.01); *G06T 2207/30024* (2013.01)

(58) Field of Classification Search
CPC .................................... A61K 31/167
USPC .................................... 424/277.1
See application file for complete search history.

(56) References Cited

U.S. PATENT DOCUMENTS

| 3,470,373 A | 9/1969 | Brewer |
| 3,497,690 A | 2/1970 | Wheeless, Jr. |
| 3,560,754 A | 2/1971 | Kamenstsky et al. |
| 3,598,471 A | 8/1971 | Baldwin |
| 3,657,537 A | 4/1972 | Wheeless, Jr. |
| 3,705,771 A | 12/1972 | Friedman et al. |
| 3,748,468 A | 7/1973 | Hartman |
| 3,833,762 A | 3/1974 | Gudmundsen |
| 3,960,449 A | 6/1976 | Carlton |
| 3,999,047 A | 12/1976 | Green |
| 4,081,277 A | 3/1978 | Brault et al. |
| 4,110,043 A | 8/1978 | Eisert |
| 4,175,860 A | 11/1979 | Bacus |
| 4,183,623 A | 1/1980 | Haines |
| 4,200,353 A | 4/1980 | Hoffman |
| 4,209,827 A | 8/1980 | Duinker |
| 4,293,221 A | 10/1981 | Kay |
| 4,360,885 A | 11/1982 | Edgar |
| 4,422,146 A | 12/1983 | Yamaguchi |
| 4,657,676 A | 4/1987 | Keary |
| 4,667,830 A | 5/1987 | Nozaki, Jr. et al. |
| 4,694,342 A | 9/1987 | Klees |
| 4,702,598 A | 10/1987 | Bohmer |
| 4,714,345 A | 12/1987 | Schrader |
| 4,747,156 A | 5/1988 | Wahl |
| 4,786,165 A | 11/1988 | Yamamoto |
| 4,858,128 A | 8/1989 | Nowak |
| 4,873,653 A | 10/1989 | Grosskopf |
| 4,891,829 A | 1/1990 | Deckman |
| 4,966,576 A | 10/1990 | Schultz |
| 4,981,829 A | 1/1991 | Shutt et al. |
| 5,034,613 A | 7/1991 | Denk |
| 5,117,466 A | 5/1992 | Buican |
| 5,125,737 A | 6/1992 | Rodriguez et al. |
| 5,141,609 A | 8/1992 | Sweedler et al. |
| 5,148,502 A | 9/1992 | Tsujiuchi et al. |
| 5,159,398 A | 10/1992 | Maekawa et al. |
| 5,177,466 A | 1/1993 | Lai |
| 5,189,518 A | 2/1993 | Nishida |
| 5,281,517 A | 1/1994 | Bacus et al. |
| 5,308,990 A | 5/1994 | Takahashi et al. |
| 5,312,535 A | 5/1994 | Waska et al. |
| 5,321,501 A | 6/1994 | Swanson et al. |
| 5,333,164 A | 7/1994 | Tam |

(Continued)

FOREIGN PATENT DOCUMENTS

| EP | 1704874 A2 | 9/2006 |
| JP | 32085747 A | 3/1990 |

(Continued)

OTHER PUBLICATIONS

Meyer et al (Cancer Cytopathol, 2015, 123(9): 512-523).*

(Continued)

*Primary Examiner* — Sean E Aeder
(74) *Attorney, Agent, or Firm* — George A. Leone

(57) ABSTRACT

A method of treating a malignancy in a human subject by analyzing pseudo-projection images of cells obtained from a sputum specimen obtained from a subject employs a biological specimen classifier that identifies cells from the sputum specimen as normal or abnormal. If abnormal cells are detected, then the abnormal cells are further classified as dysplastic or cancerous. If the cells are classified as dysplastic, then an immunomodulating agent is administered to the subject over a predetermined time period designed to achieve a therapeutic dosage.

4 Claims, 10 Drawing Sheets

(56) References Cited

U.S. PATENT DOCUMENTS

| | | |
|---|---|---|
| 5,390,226 A | 2/1995 | Tam |
| 5,402,460 A | 3/1995 | Johnson |
| 5,421,330 A | 6/1995 | Thirion |
| 5,428,447 A | 6/1995 | Toida |
| 5,496,850 A | 3/1996 | Mutoh et al. |
| 5,539,800 A | 7/1996 | Katsevich |
| 5,545,671 A | 8/1996 | Schneider et al. |
| 5,547,849 A | 8/1996 | Edgar |
| 5,548,395 A | 8/1996 | Kosaka |
| 5,550,892 A | 8/1996 | Katsevich |
| 5,552,605 A | 9/1996 | Arata |
| 5,630,938 A | 5/1997 | Feller |
| 5,644,388 A | 7/1997 | Maekawa et al. |
| 5,668,887 A | 9/1997 | Parker et al. |
| 5,673,300 A | 9/1997 | Reckwerdt |
| 5,676,631 A | 10/1997 | Kunz |
| 5,680,484 A | 10/1997 | Ohyama et al. |
| 5,689,590 A | 11/1997 | Shirasawa et al. |
| 5,710,429 A | 1/1998 | Alfano et al. |
| 5,739,540 A | 4/1998 | Motomura |
| 5,741,411 A | 4/1998 | Yeung et al. |
| 5,757,981 A | 5/1998 | Kawakubo |
| 5,760,901 A | 6/1998 | Hill |
| 5,760,951 A | 6/1998 | Dixon et al. |
| 5,768,440 A | 6/1998 | Campanelli et al. |
| 5,771,070 A | 6/1998 | Ohzu et al. |
| 5,786,893 A | 7/1998 | Fink et al. |
| 5,799,101 A | 8/1998 | Lee |
| 5,828,408 A | 10/1998 | Mottin et al. |
| 5,831,723 A | 11/1998 | Kubota et al. |
| 5,835,617 A | 11/1998 | Ohta et al. |
| 5,848,123 A | 12/1998 | Strommer |
| 5,848,181 A | 12/1998 | Ogata |
| 5,878,103 A | 3/1999 | Sauer et al. |
| 5,880,838 A | 3/1999 | Marx et al. |
| 5,909,476 A | 6/1999 | Cheng et al. |
| 5,915,048 A | 6/1999 | Hill et al. |
| 5,926,224 A | 7/1999 | Nagasawa |
| 5,978,497 A | 11/1999 | Lee |
| 5,987,158 A | 11/1999 | Meyer |
| 6,002,480 A | 12/1999 | Krantz |
| 6,005,617 A | 12/1999 | Shimamoto et al. |
| 6,026,174 A | 2/2000 | Palcic |
| 6,028,957 A | 2/2000 | Katori et al. |
| 6,037,579 A | 3/2000 | Chan et al. |
| 6,038,067 A | 3/2000 | George |
| 6,047,080 A | 4/2000 | Chen et al. |
| 6,072,624 A | 6/2000 | Dixon et al. |
| 6,078,681 A | 6/2000 | Silver |
| 6,091,983 A | 7/2000 | Alfano et al. |
| 6,130,958 A | 10/2000 | Rohler et al. |
| 6,165,734 A | 12/2000 | Garini |
| 6,177,277 B1 | 1/2001 | Soini |
| 6,192,144 B1 | 2/2001 | Holz |
| 6,201,628 B1 | 3/2001 | Basiji |
| 6,211,955 B1 | 4/2001 | Basiji |
| 6,215,587 B1 | 4/2001 | Alfano et al. |
| 6,239,871 B1 | 5/2001 | Gilby |
| 6,248,988 B1 | 6/2001 | Krantz |
| 6,249,341 B1 | 6/2001 | Basiji |
| 6,251,586 B1 | 6/2001 | Mulshine |
| 6,251,615 B1 | 6/2001 | Oberhardt |
| 6,252,979 B1 | 6/2001 | Lee |
| 6,256,096 B1 | 7/2001 | Johnson |
| 6,291,824 B1 | 9/2001 | Battarbee |
| 6,295,384 B1 | 9/2001 | Into |
| 6,312,914 B1 | 11/2001 | Kardos et al. |
| 6,330,106 B1 | 12/2001 | Greenwald et al. |
| 6,365,367 B1 | 4/2002 | Friedman et al. |
| 6,374,128 B1 | 4/2002 | Toida |
| 6,388,809 B1 | 5/2002 | MacAulay |
| 6,433,822 B1 | 8/2002 | Clark et al. |
| 6,442,235 B2 | 8/2002 | Koppe et al. |
| 6,452,179 B1 | 9/2002 | Coates et al. |
| 6,463,182 B1 | 10/2002 | Onishi et al. |
| 6,473,176 B2 | 10/2002 | Basiji |
| 6,485,413 B1 | 11/2002 | Boppart et al. |
| 6,512,807 B1 | 1/2003 | Pohlman et al. |
| 6,519,355 B2 | 2/2003 | Nelson |
| 6,522,775 B2 | 2/2003 | Nelson |
| 6,529,614 B1 | 3/2003 | Chao et al. |
| 6,532,310 B1 | 3/2003 | Into |
| 6,540,895 B1 | 4/2003 | Spence et al. |
| 6,542,573 B2 | 4/2003 | Schomberg |
| 6,591,003 B2 | 7/2003 | Chu et al. |
| 6,624,930 B1 | 7/2003 | Danner et al. |
| 6,608,682 B2 | 8/2003 | Ortyn et al. |
| 6,621,937 B1 | 9/2003 | Adams, Jr. et al. |
| 6,636,623 B2 | 10/2003 | Nelson et al. |
| 6,640,014 B1 | 10/2003 | Price et al. |
| 6,640,017 B1 | 10/2003 | Price et al. |
| 6,646,246 B1 | 11/2003 | Gindele et al. |
| 6,667,766 B2 | 12/2003 | Matsutani et al. |
| 6,697,508 B2 | 2/2004 | Nelson |
| 6,770,893 B2 | 3/2004 | Nelson |
| 6,741,730 B2 | 5/2004 | Rahn et al. |
| 6,741,752 B1 | 5/2004 | Yang |
| 6,755,969 B2 | 6/2004 | Kirker |
| 6,763,142 B2 | 7/2004 | Dai et al. |
| 6,775,399 B1 | 8/2004 | Jiang |
| 6,801,672 B1 | 10/2004 | Thomas |
| 6,823,204 B2 | 11/2004 | Grass et al. |
| 6,842,297 B2 | 1/2005 | Dowski, Jr. |
| 6,850,587 B1 | 2/2005 | Karimi |
| 6,868,177 B1 | 3/2005 | Camahort |
| 6,904,163 B1 | 6/2005 | Fujimura et al. |
| 6,931,160 B2 | 8/2005 | Gindele et al. |
| 6,937,772 B2 | 8/2005 | Gindele et al. |
| 6,944,322 B2 | 9/2005 | Johnson et al. |
| 6,975,400 B2 | 12/2005 | Ortyn et al. |
| 6,985,232 B2 | 1/2006 | Sezginer |
| 6,991,738 B1 | 1/2006 | Fauver |
| 7,003,143 B1 | 2/2006 | Hewitt |
| 7,039,455 B1 | 5/2006 | Brosovidh et al. |
| 7,050,087 B2 | 5/2006 | Harari |
| 7,050,650 B2 | 5/2006 | Maurer et al. |
| 7,075,647 B2 | 7/2006 | Chistodoulou |
| 7,092,017 B2 | 8/2006 | Kelly et al. |
| 7,113,647 B2 | 9/2006 | Nara |
| 7,136,100 B1 | 11/2006 | Kato et al. |
| 7,141,773 B2 | 11/2006 | Kaplan et al. |
| 7,173,261 B2 | 2/2007 | Ogawa et al. |
| 7,197,355 B2 | 3/2007 | Nelson |
| 7,218,393 B2 | 5/2007 | Sharpe et al. |
| 7,224,540 B2 | 5/2007 | Olmstead et al. |
| 7,253,627 B1 | 8/2007 | Ahmed |
| 7,260,253 B2 | 8/2007 | Rahn et al. |
| 7,274,809 B2 | 9/2007 | Macaulay et al. |
| 7,276,490 B1 | 10/2007 | Tanabe et al. |
| 7,280,135 B2 | 10/2007 | Kim |
| 7,362,911 B1 | 4/2008 | Frank |
| 7,391,447 B2 | 6/2008 | Lee et al. |
| 7,433,537 B2 | 10/2008 | Sasada |
| 7,440,535 B2 | 10/2008 | Netsch et al. |
| 7,443,431 B2 | 10/2008 | Kelly et al. |
| 7,479,993 B2 | 1/2009 | Nakajima et al. |
| 7,494,809 B2 | 2/2009 | Nelson et al. |
| 7,505,549 B2 | 3/2009 | Ohishi et al. |
| 7,505,551 B2 | 3/2009 | Grass et al. |
| 7,508,982 B2 | 3/2009 | Tsuyuki et al. |
| 7,518,647 B2 | 4/2009 | Kim et al. |
| 7,539,529 B2 | 5/2009 | Schmitt et al. |
| 7,542,597 B2 | 6/2009 | Rahn et al. |
| 7,569,789 B2 | 8/2009 | Hayenga et al. |
| 7,738,945 B2 | 6/2010 | Fauver et al. |
| 7,787,112 B2 | 8/2010 | Rahn et al. |
| 7,811,825 B2 | 10/2010 | Fauver et al. |
| 7,835,561 B2 | 11/2010 | Meyer et al. |
| 7,867,778 B2 | 1/2011 | Hayenga et al. |
| 7,907,765 B2 | 3/2011 | Fauver et al. |
| 7,933,010 B2 | 4/2011 | Rahn et al. |
| 8,090,183 B2 | 1/2012 | Meyer et al. |
| 8,143,600 B2 | 3/2012 | Seibel et al. |
| 8,155,420 B2 | 4/2012 | Meyer et al. |

(56) References Cited

U.S. PATENT DOCUMENTS

| | | |
|---|---|---|
| 8,254,023 B2 | 8/2012 | Watson et al. |
| 8,368,035 B2 | 2/2013 | Seibel et al. |
| 8,623,917 B2 | 1/2014 | Keith et al. |
| 8,947,510 B2 | 2/2015 | Meyer et al. |
| 2001/0012069 A1 | 8/2001 | Derndinger et al. |
| 2001/0040094 A1 | 11/2001 | Kardos et al. |
| 2002/0045525 A1 | 4/2002 | Marziali |
| 2002/0045817 A1 | 4/2002 | Ichihashi |
| 2002/0106051 A1 | 8/2002 | Menhardt |
| 2002/0122167 A1 | 9/2002 | Riley et al. |
| 2002/0141625 A1 | 10/2002 | Nelson |
| 2002/0161534 A1 | 10/2002 | Adler et al. |
| 2002/0173034 A1 | 11/2002 | Barbera-Guillem |
| 2003/0049841 A1 | 3/2003 | Short et al. |
| 2003/0063384 A1 | 4/2003 | Dowski, Jr. |
| 2003/0108512 A1 | 6/2003 | Shorr et al. |
| 2003/0118223 A1 | 6/2003 | Rahn |
| 2003/0137669 A1 | 7/2003 | Rollins et al. |
| 2003/0199758 A1 | 10/2003 | Nelson |
| 2003/0210760 A1 | 11/2003 | Nelson |
| 2003/0210814 A1 | 11/2003 | Nelson |
| 2003/0222197 A1 | 12/2003 | Reese |
| 2003/0235840 A1 | 12/2003 | Ward et al. |
| 2004/0001618 A1 | 1/2004 | Johnson |
| 2004/0008515 A1 | 1/2004 | Brown |
| 2004/0036875 A1 | 2/2004 | Kramer |
| 2004/0076319 A1 | 4/2004 | Fauver |
| 2004/0197839 A1 | 4/2004 | Daniely et al. |
| 2004/0217256 A1 | 11/2004 | Ortyn et al. |
| 2004/0228520 A1 | 11/2004 | Dresser |
| 2005/0006595 A1 | 1/2005 | Goodwin et al. |
| 2005/0010108 A1 | 1/2005 | Rahn |
| 2005/0085540 A1 | 4/2005 | Phares et al. |
| 2005/0085708 A1 | 4/2005 | Fauver |
| 2005/0085721 A1 | 4/2005 | Fauver et al. |
| 2005/0248837 A1 | 11/2005 | Sase et al. |
| 2005/0270425 A1 | 12/2005 | Min |
| 2006/0023219 A1 | 2/2006 | Meyer |
| 2006/0066837 A1 | 3/2006 | Ortyn et al. |
| 2006/0068371 A1 | 3/2006 | Ortyn et al. |
| 2006/0093200 A1 | 5/2006 | Sharpe et al. |
| 2006/0099707 A1 | 5/2006 | Nelson |
| 2006/0171041 A1 | 8/2006 | Olmstead et al. |
| 2006/0183220 A1 | 8/2006 | Nelson |
| 2006/0188869 A1 | 8/2006 | Zeskind et al. |
| 2006/0204071 A1 | 9/2006 | Ortyn et al. |
| 2006/0096358 A1 | 12/2006 | Fauver |
| 2007/0036418 A1 | 2/2007 | Pan et al. |
| 2007/0071357 A1 | 3/2007 | Rahn |
| 2007/0146673 A1 | 6/2007 | Ortyn et al |
| 2007/0146873 A1 | 6/2007 | Ortyn et al. |
| 2007/0211918 A1 | 9/2007 | Weng et al. |
| 2007/0215528 A1 | 9/2007 | Hayenga |
| 2007/0238957 A1 | 10/2007 | Yared |
| 2007/0258122 A1 | 11/2007 | Chamgoulov et al. |
| 2008/0151081 A1 | 6/2008 | Frank |
| 2008/0175455 A1 | 7/2008 | John et al. |
| 2008/0194946 A1 | 8/2008 | Summers et al. |
| 2008/0239110 A1 | 10/2008 | Hara |
| 2008/0285827 A1 | 11/2008 | Meyer et al. |
| 2009/0103792 A1 | 4/2009 | Rahn et al. |
| 2010/0296713 A1 | 11/2010 | Meyer |
| 2012/0191635 A1 | 7/2012 | Bigio |
| 2014/0296089 A1 | 10/2014 | Holmes |
| 2015/0104786 A1 | 4/2015 | Shirasuna |
| 2017/0003267 A1 | 1/2017 | Meyer et al. |

FOREIGN PATENT DOCUMENTS

| | | |
|---|---|---|
| JP | 10260131 A | 9/1998 |
| JP | 2000121550 A | 4/2000 |
| WO | WO0111341 A2 | 2/2002 |
| WO | WO0218537 A2 | 3/2002 |
| WO | WO0235474 A1 | 5/2002 |
| WO | WO02095476 A2 | 11/2002 |
| WO | WO 03/072059 | 9/2003 |
| WO | WO 2004/017993 | 3/2004 |
| WO | WO 2006/008437 | 1/2006 |
| WO | 2006016290 A1 | 2/2006 |
| WO | WO 2008/088617 | 7/2008 |

OTHER PUBLICATIONS

Meyer et al (Pattern Recognition, 2009, 42: 141-146).*
Neumann et al (Cancer Cytopathology, 2009, 473-481).*
Marsh et al (Cancer, 1976, 37: 437-439).*
Keith et al (Cancer Prev Res, 2011,4(6): 793-802).*
Urbine et al (J Clin Oncol, 2012, ASCO Annual Meeting, Abstract e17529).*
Nelson et al (J Clin Oncol, 2014, ASCO Annual Meeting, Abstract 7547).*
Nandakumar et al (Cytometry, 2011, 79(1): 25-34).*
Asaoka et al (Invest Ophthalmol Vis Sci, 2014, 55(4): 2482-2490).*
Gray et al (NeuroImage, 2013, 65:167-175).*
Wu et al (Chin Med J, 2008, 121(24): Abstract).*
Lunetta et al (BMC Genetics, 2004, 5(32): 1-13).*
Cutler et al (Methods Enzymol, 2006, 411: 422-432).*
Feridex I.V. (Ferumoxides Injectable Solution), May 2007 Bayer HEalth Pharaceuticles Inc.
Kieth, Robert et al.,"Oral Iloprost Improves Endobronchial Dysplasia in Former Smokers", Cancer Prev Res (Phila). Jun. 2011 ; 4(6): 793-802. doi:10.1158/1940-6207.CAPR-11-0057.
D'Amelio, Patrizia et al.,"Iloprost modulates the immune response in systemic sclerosis," D'Amelio et al. BMC Immunology 2010, 11:62.
Rosenberg, Steven A., "IL-2: The First Effective Immunotherapy for Human Cancer", J Immunol 2014; 192:5451-5458; doi: 10.4049/jimmunol.1490019.
Tsuruo, Takashi and Fujita, Naoya, "Platelet aggregation in the formation of tumor metastasis", Proc. Jpn. Acad., Ser. B 84 (2008).
U.S. Appl. No. 10/126,026, "Non-Final Office Action", dated Jun. 30, 2005.
U.S. Appl. No. 10/126,026,"Amendment/Reply", dated Sep. 20, 2005.
U.S. Appl. No. 10/126,026,"Notice of Allowability", dated Feb. 22, 2006.
CA App. No. 2482920, "Examiner's Report", dated Oct. 24, 2011.
CA App. No. 2482920, "Amendment/Remarks After Examiner's Report", dated Apr. 24, 2012.
CA App. No. 2482920, "Examiner's Report", dated Aug. 15, 2011.
CA App. No. 2482920, "Amendment/Remarks After Examiner's Report", dated Oct. 8, 2011.
CA App. No. 2482920, "Examiner's Report", dated Feb. 17, 2014.
CA App. No. 2482920, "Amendment/Remarks After Examiner's Report", dated Jun. 25, 2014.
EP App. No. 3751595, "Supplementary Search Report", dated Sep. 1, 2010.
EP App. No. 3751595, "Communication Pursuant to Article 94(3) EPC", dated Dec. 3, 2010.
EP App. No. 3751595, "Communication Pursuant to Article 94(3) EPC", dated Jun. 6, 2011.
EP App. No. 3751595, "Invitation Pursuant to Article 94(3) and Rule 71(1) EPC" dated Jan. 7, 2015.
EP App. No. 3751595, "Response" dated Apr. 21, 2015.
EP App. No. 3751595, "Communication Under Rule 71(1) EPC" dated Jan. 8, 2016.
International App. No. PCT/2003/010901, "International Search Report", dated Jun. 23, 2004.
International App. No. PCT/2003/010901, "International Preliminary Report on Patentability" dated Aug. 9, 2004.
International Appl No. PCT/2003/013674, "International Search Report", dated Jul. 24, 2003.
International Appl No. PCT/2003/013674, "International Preliminary Report on Patentability" dated Dec. 27, 2003.
CA App. No. 2485576, "Examiner's Report", dated Jun. 1, 2011.
CA App. No. 2485576, "Amendment/Remarks After Examiner's Report", dated Dec. 1, 2011.
EP App. No. 03728655.6, "Search Report", dated Apr. 21, 2010.

(56) References Cited

OTHER PUBLICATIONS

EP App. No. 03728655.6, "Supplementary Search Report", dated Apr. 21, 2010.
EP App. No. 03728655.6, "Communication Pursuant to Article 94(3) EPC", dated Aug. 9, 2010.
EP App. No. 03728655.6, "Response Pursuant to Article 94(3) EPC", dated Feb. 7, 2011.
EP App. No. 03728655.6, "Intention to Grant", dated Dec. 11, 2015.
U.S. Appl. No. 1030809, "Non-Final Office Action", dated May 6, 2004.
U.S. Appl. No. 1030809, "Amendment in Response to Office Action", dated Nov. 23, 2004.
U.S. Appl. No. 1030809, "Notice of Allowability", dated Mar. 17, 2005.
CA App. No. 2504787, "Examiner's Report", dated Feb. 3, 2011.
CA App. No. 2504787, "Amendment/Remarks Following Examiner's Report", dated Aug. 3, 2011.
EP App. No. 03790059.4, "Communication Pursuant to Article 94(3) EPC", dated Sep. 22, 2016.
EP App. No. 03790059.4, "Response Pursuant to Article 94(3) EPC", dated Jan. 20, 2017.
International Appl No. PCT/US2003/037713, "International Search Report", dated Oct. 1, 2004.
International Appl No. PCT/US2003/037713 "International Preliminary Report on Patentability" dated Dec. 3, 2004.
U.S. Appl. No. 10/716,744, "Non-Final Office Action", dated Jun. 25, 2009.
U.S. Appl. No. 10/716,744, "Statement of the Substance of the Interview", dated Sep. 1, 2009.
U.S. Appl. No. 10/716,744, "Response with Amendments and Election of Claims", dated Sep. 1, 2009.
U.S. Appl. No. 10/716,744, "Supplemental Notice of Allowability", dated Apr. 15, 2010.
International Appl No. PCT/US04/037323, "International Search Report", dated Feb. 5, 2007.
International Appl No. PCT/US04/037323, "Written Opinion of the International Searching Authority", dated Feb. 5, 2007.
International Appl No. PCT/US04/037323, "International Preliminary Report on Patentability", dated Jul. 9, 2007.
U.S. Appl. No. 10/964,508, "Non-Final Office Action", dated Jul. 7, 2009.
U.S. Appl. No. 10/964,508, Response Under 37 CFR 3.111, dated Oct. 2, 2009.
U.S. Appl. No. 11/421,873, "Response", dated Oct. 22, 2010.
U.S. Appl. No. 11/421,873, "Advisory Action", dated Nov. 17, 2010.
U.S. Appl. No. 11/421,873, "Non-Final Office Action", dated Jan. 13, 2011.
U.S. Appl. No. 11/421,873, "Response", dated Jul. 13, 2011.
U.S. Appl. No. 11/421,873, "Non-Final Office Action", dated Sep. 23, 2011.
U.S. Appl. No. 11/421,873, "Amendment and Response", dated Mar. 23, 2012.
U.S. Appl. No. 11/421,873, "Final Office Action", dated Jul. 13, 2012.
U.S. Appl. No. 11/421,873, "Amendment and Response", dated Jan. 11, 2013.
U.S. Appl. No. 11/421,873, "Interview Summary", dated Sep. 27, 2013.
U.S. Appl. No. 11/421,873, "Notice of Allowability", dated Sep. 27, 2013.
European Application No. 06784582.2, "European Search Report," dated May 8, 2009.
International Application No. PCT/US06121666,"Written Opinion of the International Searching Authority," dated Apr. 19, 2007.
International Application No. PCT/US06/21666,"International Search Report," dated Apr. 19, 2007.
International Application No. PCT/US06/21666,"International Preliminary Report on Patentability," dated Dec. 6, 2007.
U.S. Appl. No. 10/964,508, "Notice of Allowability", dated Jul. 12, 2010.
U.S. Appl. No. 10/876,328, "Final Office Action", dated Feb. 24, 2006.
U.S. Appl. No. 10/876,328, "Response to Non-Final Office Action", dated Apr. 27, 2006.
U.S. Appl. No. 10/876,328, "Non-Final Office Action", dated Jun. 12, 2006.
U.S. Appl. No. 10/876,328, "Response to Final Office Action", dated Jun. 26, 2006.
U.S. Appl. No. 10/876,328, "Advisory Action", dated Jul. 7, 2006.
U.S. Appl. No. 10/876,328, "Request for Continued Examination", dated Sep. 8, 2006.
U.S. Appl. No. 10/876,328, "Supplemental Notice of Allowability", dated Nov. 13, 2006.
U.S. Appl. No. 11/558,593, "Non-Final Office Action", dated Sep. 26, 2008.
U.S. Appl. No. 11/558,593, "Response under 37 CFR 1.111", dated Dec. 15, 2008.
U.S. Appl. No. 11/558,593, "Notice of Allowability", dated Jan. 9, 2009.
International App. No. PCT/US2005/019847, "Written Opinion of the International Searching Authority", dated Aug. 17, 2006.
International App. No. PCT/US2005/019847, "International Search Report", dated Aug. 17, 2006.
International App. No. PCT/US2005/019847, "International Preliminary Examination Report", dated Jan. 25, 2007.
CA App. No. 2570730,"Examiner's Report", dated Mar. 14, 2012.
CA App. No. 2570730,"Amendment/Remarks After Examiner's Report", dated Sep. 11, 2012.
European App. No. 05757464.2, "Supplementary European Search Report", dated Oct. 5, 2012.
European App. No. 05757464.2, "Communication Pursuant to Article 94(3) EPC", dated Dec. 13, 2012.
European App. No. 05757464.2, "Response to the Communication Pursuant to Article 94(3) EPC", dated Jun. 11, 2013.
European App. No. 05757464.2, "Communication Pursuant to Article 94(3) EPC", dated Feb. 6, 2014.
European App. No. 05757464.2, "Communication Pursuant to Article 94(3) EPC", dated Oct. 30, 2014.
European App. No. 05757464.2, "Response to the Communication Pursuant to Article 94(3) EPC", dated Feb. 13, 2015.
European App. No. 05757464.2, "Intention to Grant", dated Jun. 8, 2015.
U.S. Appl. No. 11/532,648, "Non-Final Office Action", dated May 11, 2010.
U.S. Appl. No. 11/532,648, "Response Under 37 CFR 1.111", dated Aug. 10, 2010.
U.S. Appl. No. 11/532,648, "Notice of Allowability", dated Nov. 1, 2010.
International App. No. PCT/US07/78206, "Written Opinion of the International Searching Authority", dated Mar. 15, 2008.
International App. No. PCT/US07/78206, "Search Report", dated Mar. 15, 2008.
International App. No. PCT/US07/78206, "International Preliminary Report on Patentability", dated Mar. 15, 2008.
Australian Application No. 2007297473, "Examiner's Report", dated Mar. 4, 2013.
Australian Application No. 2007297473, "Response to Examiner's Report", dated Sep. 30, 2013.
Australian Application No. 2007297473, "Notice of Acceptance", dated Nov. 4, 2013.
CA App. No. 2663744,"Examiner's Report", dated Apr. 2, 2014.
CA App. No. 2663744,"Response to Examiner's Report", dated Sep. 22, 2014.
CA App. No. 2663744,"Examiner's Report", dated May 1, 2015.
CA App. No. 2663744,"Response to Examiner's Report", dated Aug. 10, 2015.
European App. No. 07842287.0 , "European Search Opinion", dated Jan. 7, 2014.
European App. No. 07842287.0 , "Supplementary Search Report", dated Dec. 18, 2013.

(56) References Cited

OTHER PUBLICATIONS

European App. No. 07842287.0 , "Response to Communication pursuant to Rules 70(2) and 70a(2) EPC", dated Jul. 21, 2014.
U.S. Appl. No. 11/750,924, "Interview Summary", dated Jul. 30, 2010.
U.S. Appl. No. 11/750,924, "Notice of Allowability", dated Jul. 30, 2010.
International App. No. PCT/US08/63548, "Written Opinion of the International Searching Authority", dated Aug. 8, 2008.
International App. No. PCT/US08/63548, "International Search Report", dated Aug. 8, 2008.
International App. No. PCT/U508/63548, "International Preliminary Report on Patentability", dated Nov. 24, 2009.
U.S. Appl. No. 12/391,096, "Non-Final Office Action", dated Nov. 7, 2011.
U.S. Appl. No. 12/391,096, "Response Under 37 CFR 1.111", dated Feb. 3, 2012.
U.S. Appl. No. 12/391,096, "Notice of Allowability", dated Apr. 30, 2012.
International App. No. PCT/US2010/024959, "Written Opinion of the International Searching Authority", dated Oct. 14, 2010.
International App. No. PCT/US2010/024959, "International Search Report", dated Oct. 14, 2010.
International App. No. PCT/US2010/024959, "International Preliminary Report on Patentability", dated Aug. 23, 2011.
Farichild Imaging, Preliminary Data Sheet CCD582, TDI, Time Delay and Integration Sensor, Jan. 18, 2000.
Kikuchi, S. et al., "Three-Dimensional Computed Tomography for optical microscopes," Optics Communications 107 432-444, 1994.
Kikuchi, S. et al., "Three-Dimensional Microscopic Computed Tomography based on General Radon Transform for Optical Imaging Systems," Optics Communications 123, 1996.
Matula, P. et al., "Precise 3D Image Alignment in Micro-Axial Tomography," Journal of Microscopy, vol. 209, Pt. 2 (Feb. 2003) pp. 126-142.
W.H. Press et al., Numeric Recipes in C, New York; Cambridge University Press, 1988.
Reymond and Pickett-Heaps,"A Routine Flat Embedding Method for Electron Microscopy of Microorganisms Allowing Selection and Precisely Orientated Sectioning of Single Cells by Light Microscopy," Journal of Microscopy, vol. 130 Pt. 1 Apr. 19833 pp. 79-84.
Nicewarner-Pena et al.,"Submicrometer Metallic Barcodes," Science 294 137, 2001.
Polymicro Technologies, "Square Flexible Fused Silica Capillary Tubing," www.polymicro.com, 2003.
Shannon, The Art and Science of Optical Design, 1977, University of Arizona, Cambridge University Press, Fig. 4.12 and Fig. 4.13.
Fauver et al., "Development of Micro-Optical Projection Tomography for 3D Analysis of Single Cells, Image Acquisition and Processing XI." Edited by Conchello, Jose-Angel; Cogswell, Carol J.; Wilson, Tony. Proceedings of the SPIE, vol. 5324, pp. 171-181, 2004.
Zaidi, H. and Hasegawa, B., Determination of the Attenuation Map in Emission Tomography, The Journal of Nuclear Medicine, Special Contributions, vol. 44, No. 2, Feb., 291-315, 2003.
Fauver et al., "Three-dimensional imaging of single isolated cell nuclei using optical projection tomography," Optics Express, May 30, 2005/vol. 13, No. 11/4210-4223.
Pieper, R. J. and Korpel A., Image processing for extended depth of field, Applied Optics, vol. 22, No. 10, May 15, pp. 1449-1453, 1983.
Bradburn S. et al., Realization of focus Invariance in Optical/Digital Systems with Wavefront Coding, Applied Optics, vol. 36, Issue 35, pp. 9157-9166, 1997.
Sheppard, C. J. R. and Torok, P., Effects of specimen refractive index on confocal imaging, Journal of Microscopy, vol. 185, Pt. 3, Mar. 1997, pp. 366-374.
Tucker, S. C. et al., Extended depth of field and aberration control for inexpensive digital microscope systems, Optics Express, vol. 4, No. 11, May 24, pp. 467-474, 1999.

Edelmann, P. et al., "Correlation of chromatic shifts and focal depth in spectral precision distance microscopy measured by micro axial tomography," Optical Biopsies and Microscopic Techniques III, Sep. 1999, SPIE vol. 3568, pp. 89-95.
Widjanarko, T., et al., "A post-processing technique for extending dpth of focus in conventional optical micorscopy," Optics & Laser Technology 34, pp. 299-305, 2002.
Martini, N et al., "A new high-aperture glycerol immersion objective lens and its application to 3D-flouresence microscopy," Journal of Microscopy vol. 206 Pt. 2, May 2002, pp. 146-151, 2002.
Lane, P. M. et al.,"Confocal Microendoscopy with chromatic sectioning," Spectral Imaging: Instrumentation, Applications, and Analysis II, Proc. of SPIE vol. 4959 pp. 23-26, 2003.
Berge, B et al.,"Liquid Lens Technology: Principle of Electrowetting Based Lenses and Applications to Imaging," Micro Electro Mechanical Systems, Jan. 30- Feb. 3, 2005, MEMS 2005, 18th IEEE International Conference on, p. 227-230.
Gabay, C. et al., "Dynamics Study of Varioptic Variable Focal Lenses," Proc. SPIE, vol. 4767, 159 (2002); DOI: 10, 1117/12. 4682224.
Physik Instrumente,"P-725 PIFOC(R) Long-Travel Objective Scanner High-Precision Positioner/Scanner for Microscope Objectives," 2008, http://www.physikinstrumente.com/en/products/prdetail.php?sortnr=200375.
Porras, R. et al.,"Waverfont coding technology in the optical design of astronomical instruments," 5th Iberoamerican Meeting on Optics and 8th Latin American Meeting on Optics, Lasers and Their Applications, Edited by A Marcano o., J.L. Paz, Proc. of SPIE (2004) vol. 5622, pp. 796-800.
Forster, B. et al., "Complex Wavelets for Extended Depth-of-field: A New Method for the Fusion of Multichannel Microscopy Images," Microscopy Research and Technique, 2004, 65:33-42.
Miks, A. et al., "Theory of hyperchromats with linear longitudinal chromatic, aberration," Proc. of SPIE, 2005, vol. 5945, pp. 59450, Y1-Y8.
Abrahamsson, S. et al.,"A new approach to extended focus for high-speed, high resolution biological microscopy," Proc. of SPIE (2006) vol. 60900, N1-N8.
Chang, et al.,"Enhanced live cell membrane imaging using surface plasmon-enhanced total internal reflection fluorescence microscopy," Optics Express 9308, vol. 14, No. 20, Oct. 2, 2006.
Curry A. et al., "Epi-illumination through the microscope objective applied to darktield imaging and microspectroscopy of nanoparticle," Jul. 10, 2006, vol. 14, No. 14, Optics Express 6535.
Leitgeb, R. et al,"Extended focus depth for Fourier domain optical coherence microscopy," Optics Letters, Doc. ID 69650, Jun. 2006.
Mikula, G. et al., "Imaging with extended focal depth by means of lenses with radial and angular modulation," Optics Express, Jul. 23, 2007, vol. 15, No. 15, pp. 9184-9193.
Xu, Y. et al., "Ultra long high resolution beam by multi-zone rotationally symmetrical complex pupil filter," Optics Express, May 10, 2007, vol. 15, No. 10, pp. 6409-6413.
Conchello, J-A. et al., "Extended depth-of-focus microscopy via constrained deconvolution," Journal of Biomedical Optics 12 (6), 064026 (Nov./Dec. 2007).
Somayaji, M. et al., "Enhancing form factor and light collection of multiplex imaging systems by using a cubic phase mask," Applied Optics, vol. 45, No. 13, May 2006, pp. 2911-2923.
Darrell, A. et al., "Accounting for Point Source Propagation Properties in 3D Florescence OPT," Proceedings of the 28th IEEE, EMBS Annual Internationa Conference, New York City, USA Aug. 30-Sep. 3, 2006.
Kerfoot, et al., "Quantitative Multiplex Chromagenic Immunohistochemistry," Mosaic Laboratories, (2007) www.mosaiclabs.com, Tuscan Symposium.
Long, J.C. et al. Tube Lens Focal Length, Nikon Microscopy U: INteractive Java Tutorials, (2007) www.microscopy.com.
Zesking, B.J. et al., Nucleic acid and protein mass mapping by live-cell deepultraviolet, Nature Methods, published online, 4, 567-569, Jun. 2007; DOI:101038/NMETH1053.

(56) References Cited

OTHER PUBLICATIONS

Zesking, B.J. et al., Nucleic acid and protein mass mapping by live-cell deepultraviolet, Nature Methods, published online, 4, 567-569, Jun. 2007; DOI:101038/NMETH1053 (Supplementary Figures and Text).
King, M.C. and Berry, D.H.,"A depth scanning microscope," Applied Optics, vol. 10, No. 1 Jan. 1971 pp. 208-210.
Preza, C. et al., "Three-Dimensional Transmitted-Light DIC Microscopy," Presented at SPIE's BiOS97;3D Microscopy Image Acquisition and Processing IV, 2984-24, 1997.
Marks D. L. et al., "Three-dimensional tomography using a cubic-phase plate extended depth-of-field system," Optics Letters, Feb. 15, 1999, vol. 24, No. 4.
Sanyal, S. and Ghosh, A., "High focal depth with a quasi-bifocus birefimgent lens," Applied Optics, vol. 39, No. 14, May 10, 2000 pp. 2321-2325.
Herzenberg, L.A., The History and Future of the Flouresence Activated Cell Sorter and Flow Cytometry: A View from Stanford, 2002.
Meyer, et al., "Automated cell analysis in 2D and 3D: A comparative study," Science Direct: Pattern Recognition, 2009.
Neuman, Thomas, et al., "Simultaneous 3D imaging of Morphology and nanoparticle Distribution in Single Cells with the Cell-CT Technology," Engineering in Medicine and biology Society, 2008. EMBS 2008. 30th Annual International Conference of the IEEE.
True, L. and Gao, X., "Quantum Dots for Molecular Pathology: Their Time Has Arrived," The Journal of Molecular Diagnostics, vol. 9, Issue 1, pp. 7-11, Feb. 2007.
Australian Application No. 2010215794, "Notice of Acceptance", dated Apr. 17, 2014.
European App. No. 10744448.1, "Communication pursuant to Rules 70(2) and 70a(2) EPC", dated Dec. 23, 2016.
U.S. Appl. No. 12/403,231, "Notice of Allowability", dated Oct. 21, 2011.
International Application No. PCT/US10/26862, "Written Opinion of the International Searching Authority", dated Nov. 18, 2010.
International Application No. PCT/US10/26862, "International Search Report", dated Nov. 18, 2010.
International Application No. PCT/US10/26862, "International Preliminary Report on Patentability", dated Sep. 13, 2011.
AU Application No. 2010224187,"Notice of Acceptance", dated May 28, 2014.
CA Application No. 2755056, "Examiner's Report", Jul. 15, 2016.
CA Application No. 2755056, "Response/Remarks Following Examiner's Report", dated Jan. 4, 2017.
European Application No. 10751376.4, "Extended European Search Report", dated Sep. 25, 2013.
European Application No. 10751376.4, "Response to the communication pursuant to Rules 70(2) and 70a(2) EPC", dated Mar. 7, 2014.
European Application No. 10751376.4, "Intent to Grant", dated Apr. 17, 2014.
Dresler, C., Lunc Cancer, 2003, Vo. 39, pp. 119-124.
Winterhalder et al., "Chemoprevention of lung cancer—from biology to clinical reality," Annals of Oncology, Feb. 2004, vol. 15, pp. 185-196.
Kushiro et al., "Therapeutic Effects of Prostacyclin Analog on Crescentic glomerulonephritis of rat," Kidney International, 1998, V.53, pp. 1314-1320.
Naeije et al., "Pulmonary hypertension associated with COPD," Crit. Care, 2001, V. 5(6), pp. 286-289.
Jones et al., "Pulmonary Vasodilation with prostacyclin in primary and secondary pulmonary hypertension", Chest, 1989, V. 96, pp. 784-789.
Keith et al.,"Manipulation of Pulmonary Prostacyclin Synthase Expression Prevents Murine Lung Cancer", 2002, Cancer Research, vol. 62, pp. 734-740.
Suggitt et al., "50 Years of Preclinical Anticancer Drug Screening:Empirical to Target-Driven Approaches", 2005, Clinical Cancer Research, vol. 11, pp. 971-981.

U.S. Appl. No. 12/470,413, "Non-Final Office Action", dated Aug. 18, 2011.
U.S. Appl. No. 12/470,413, "Response under 37 CFR 1.111", dated Nov. 18, 2011.
U.S. Appl. No. 12/470,413, "Notice of Allowability", dated Dec. 12, 2011.
International Application No. PCT/US10135673, "Written Opinion of the International Searching Authority", dated Dec. 23, 2010.
International Application No. PCT/US10/35673, "International Search Report", dated Dec. 23, 2010.
International Application No. PCT/US10/35673, "International Preliminary Report on Patentability", dated Nov. 22, 2011.
AU Application No. 2010249504,"Patent Examination Report No. 1", dated Nov. 17, 2014.
AU Application No. 2010249504,"Response to Patent Examination Report No. 1", dated Apr. 1, 2015.
AU Application No. 2010249504,"Notice of Acceptance", dated May 1, 2015.
CA Application No. 2762848, "Examiner's Report", dated Jun. 16, 2015.
CA Application No. 2762848, "Response to Examiner's Report", dated Oct. 22, 2015.
European Application No. 10778428.2, "Extended European Search Report", dated Jun. 3, 2013.
European Application No. 10778428.2, "Response to the communication Pursuant to 70(2) and 70a(2) EPC", dated Dec. 17, 2013.
European Application No. 10778428.2, "Intention to Grant", dated Jan. 13, 2015.
U.S. Appl. No. 12/999,515, "Non-Final Office Action", dated Mar. 27, 2014.
U.S. Appl. No. 12/999,515, "Response Under 37 CFR 1.111," dated Sep. 18, 2014.
U.S. Appl. No. 12/999,515, "Notice of Allowability", dated Oct. 6, 2014.
International Application No. PCT/US09/46558, "Written Opinion of the International Searching Authority", dated Jan. 7, 2010.
International Application No. PCT/US09/46558, "International Search Report", dated Jan. 7, 2010.
International Application No. PCT/US09/46558, "International Preliminary Report on Patentability", dated Dec. 21, 2010.
U,.S. Appl. No. 12/403,231, "Notice of Allowability", dated Dec. 7, 2016.
International Application No. PCT/US16/39591, "Written Opinion of the International Searching Authority", dated Nov. 23, 2016.
International Application No. PCT/US16/39591, "International Search Report", dated Nov. 23, 2016.
U.S. Appl. No. 11/421,873, "Non-Final Office Action", dated Apr. 15, 2008.
U.S. Appl. No. 11/421,873, "Amendment and Response", dated Oct. 15, 2008.
U.S. Appl. No. 11/421,873, "Final Office Action", dated Jan. 12, 2009.
U.S. Appl. No. 11/421,873, "Amendment and Response", dated Jun. 12, 2009.
U.S. Appl. No. 11/421,873, "Advisory Action", dated Jul. 8, 2009.
U.S. Appl. No. 11/421,873, "Non-Final Office Action", dated Dec. 18, 2009.
U.S. Appl. No. 11/421,873, "Amendment and Response", dated Mar. 17, 2010.
U.S. Appl. No. 11/421,873, "Final Office Action", dated Jun. 23, 2010.
Schmitz, "Performance Characteristics of a Silicon Photodiode (SiPD) Based Instrucment for Fast Functional Optical Tomography," Undated, SUNY Downstate Medical Center Brooklyn, NY.
Shapiro, HM, Practical Flow Cytometry, 3rd Ed., Wiley-Liss. 1995.
Gilbert, P, "Iterative Methods for the Three dimensional Reconstruction of an Object from Projections," Journal of Theoretical Biology 36:105-17, 1972.
Oppenheim, BE, "Mor Accurate Algorithms for Iterative 3 Dimensional Reconstruction," IEEE Transactions on Numclear Science NS-21:72-7, 1974.

(56) References Cited

OTHER PUBLICATIONS

Singer, JR, Grunbaum, FA, Kohn, P, and Zubelli, JP, "Image Reconstruction of the Interior of Bodies that Diffuse Radiation," Science 248(4958):990-3, 1990.

Mueller, K and Yage R, "Rapid 3-D Cone-beam Reconstruction with the Simultaneous Algebraic Reconstruction Technique (SART) Using 2-D Texture Mapping Hardware," IEEE Transactions on Medical imaging 19(12):1227-37, 2001.

Bellman, SH, Bender, R, Gordon R, and Rowe, JE, "Art is Science being a Defense of Algebraic Reconstruction Techniques for Three Dimensional Electron Microscopy," Journal of Theorectical Biology 32:205-16, 1971.

Manglos, SH, Jaszcak, RJ, and Floyd, CE, "Maximum Likelihood Reconstruction for Cone Beam SPECT: Development and Initial Tests," Physics in Medicine and Biology 34(12):1947-57, 1989, #1382.

Manglos, SH, et al., "Transmission Maximum-likelihood Reconstruction with Ordered Subsets for Cone Beam CT", Physics in Medicine and Biology 40(7):1225-41, 1995, #4389.

Hampel, U and Freyer, R, "Fast Image Reconstruction for Optical Abasortion Tomography in Media with Radially Symmetric Boundaries," Medical Physics 25(1):92-101, 1998.

Jiang, H, Paulsen, KD, and Osterberg, UL, "Frequency-Domain Near-infared Photo Diffusion Imaging:Initial Evaluation in Multitarget Tissuelike Phantoms," Medical Physics 25(2)183-93, 1998.

Herman, G, Image Reconstruction From Projections: The Fundamentals of Computerized Tomography, Academic Press, New York, 1980.

Paulsen, KD and Jiang, H, Spatially Varying Optical Property Reconstruction Using a Finite Element Diffusion Equation Approximation, Medical Physics 22(691-701) 1995.

Ong, SH, Development of an imaging flow cytometer, Anal Quant Cytol Histol 9(5)pp. 375-382, 1987.

Farichild Imaging, Preliminary Data Sheet CCD525, TDI, Time Delay and Integration Sensor, Jan. 12, 2001.

HJ Tiziani and MI Uhde, "Three-Dimensional analysis by a mocrolens array confocal arragements," Applied Optics, 33, 567 1994.

Bayat, S., et al, "Quantitative Functional Lung Imaging with Synchrotron Radiation Using Inhaled Xenon as Contrast Agent," Physics in Medicine and Biology 46 (3287-99) 2001.

Bentley, MD., et al., "The Use of Microcomputed Tomography to Study Microvasculature in Small Rodents," American Journal of Physiology (Regulatory Intergrative Comp Physiol) 282(R1267-R1279) 2002.

Cheng, PC., Et al., "Review on the Development of Cone-beam X-ray Microtomograph," Proceedings of the X-ray Optics and Microanalysis 1992, Institue of Physics Ser. No. 130, Kenway, PB, et al (eds.), Manchester UK, Aug. 31-Sep. 4, 1992, pp. 559-566.

Defrise, M., et al., "Image Reconstruction from Truncated, Two-Dimensional, Parallel Projections," Inverse Problems 11(287-313) 1995.

Defrise, M, et al., "A Solution to the Long-object Problem in Helical Conebeam Tomography," Physics in Medicine and Biology 45(623-43) 2000.

Endo, M, et al., "Effect of Scattered Radiation on Image Noise in Cone Beam CT," Medical Physics 28(4) (459-74 2001.

Jorgensen, SM, et al., "Three Dimensional Imaging of Vasculature and Parenchyma in Intact Rodent Organs with X-ray Micro-CT," Am. J. Physiology 275 (Heart Circ. Physiol 44) pp. H1103-H1114, 1998.

Kinney, JH, et. al., "Energy-modulated X-ray Microtomography," Rev. Sci. Instrum. 59(1)pp. 196-197, 1988.

Kinney, JH and Nichols, MC "X-ray Tomographic Microscopy (XTM) Using Synchrotron Raitiation," Annu. Rev. Mater. Sci. 22pp. 121-152, 1992.

Taguchi, K and Aradate, H, "Algorithm for Image Reconstruction in Multi-slice Helical CT," Medical Physics 25(4) pp. 550-561, 1998.

Yu, DF et al., "Maximum-likelihood Transmission Image Reconstruction for Overlapping Transmission Beams," IEEE Transactions on Medical Imaging 19(11) pp. 1094-1105, 2000.

Sharpe, J, Ahlgren, U et al., "Optical Projection Tomography as a Tool for 3D Micorscopy and Gene Expression Studies," Science, vol. 296, pp. 541-545, Apr. 19, 2002.

Sharpe, J, review, "Opitical Projection Tomography as a New Tool for Studying Embryo Anatomy," J. Anat. (2003), pp. 175-181.

RH Anderson, "Close-up imaging of documents and displays with lens arrays," Applied Optics 18, 477, 1979.

Kak, A.C. And Slaney, M., Principles of Computerized Tomographic Imaging, IEEE Press, New York 1988.

E. G. Steward, Fourier Optics: An Introductions, 2nd ed. Halsted Press, New York, 1987.

A. Klug and J. L. Finsch, "Structure of Viruses of Papilloma-polyoma Type," J. Mol. Niol., vol. 37, p. 1, 1968.

A. Klug, "Image analysis and reconstruction in the electron microscopy of biological macromolecules," Chen, Scripta, vol. 14, p. 245, 1978.

T.C. Wedberg and J. J. Stamnes, "Recent results in optical diffraction microtomography," Meas. Sci. Technol., vol. 7, p. 414, 1996.

Y. Li, et al. "Comparison of analog and digital Fourier Transforms in Medical Image Analysis," J. Biomed. Optics, vol. 7, p. 244, 2002.

Y. Xu et al., "Three-dimensional diffuse optical tomography of bones and joints," J. Biomed. Optics, vol. 7 p. 88, 2002.

H. Banda-Gamboa et al., "Spectral-Analysis of Cervical Cells Using the Discrete Fourier-Transform," Anal. Cell. Path., vol. 5(2), pp. 85-102, 1993.

D.E. Burger, et al.,"Extraction of Morphilogical Features from Biological Models and Cells by Fourier Analysis of Static Light Scatter Measurements," Cytometry, vol. 2, No. 5, pp. 327-336 1982.

M. Rozycka, et al.,"Optical Diffration as a Tool for Semiautomatic, Quantitative Analysis of Tissue Specimens," Cytometry. vol. 2, No. 4, pp. 244-248 1982.

Almeida and Fuji, "Fourier Transform Differences and Averaged Simularities in Diatoms," Applied Optics, vol. 18, No. 10, pp. 1663-1667, 1997.

Miles, CP, Jaggard, DL,"The Use of Optical Fourier Trnsforms to Diagnose Pleomorphism, Size and Chromatin Clumping in Nuclear Models," Anal Quant Cytol Histol vol. 3, No. 2, pp. 149-156, 1981.

Dziedzic-Goclowska, et al.,"Application of the Optical Fourier Transform for Analysis of the Spatial Distribution of Collagen Fibers in Normal Osteopetrotic Bone Tissue," Histochemistry 74:123-137, 1982.

Ostrowski, et al.,"Application of Optical Diffractometry in Studies of Cell Fine Structure," Histochemistry 78:435-449, 1982.

Mareel, MM, et al.,"Numerical Evaluation of Changes in the Cytoplasmic Microtubule Complex of C3H Mouse Cells by Optical Diffractometry and of Changes in Cell Shape by Fourier Analysis," Cytometry 7:18-24, 1986.

Bem, W, et al., "Modification of Chromatin Pattern in the Course of Terminal Differentiation During Human Granulocytopiesis: Optical Diffractometry Study," Cellular and Molecular Biology 33(5), 563-571, 1987.

Rozycka, M, et al.,"Analysis of Chromatin Pattern in Blood Lymphocytes of Healthy Donors and Lymphoid Cells of Patients with Chronic Lymphocytic Leukemia," J. Clin. Pathol. 1988:44:504-509.

George, JS et al., "Virtual Pinhole Confocal Microscope," Physics Divsion Progress Report, www.lanl.gov/p/pdf/papp_pinhole.pdf, 1999-2000.

Schmitz, "Performance Characteristics of a Silicon Photodiode (SiPD) Based Instrucment for Fast Functional Optical Tomography," Undated, SUNY Downstate Medical Center Brooklyn, NY, Jun. 29, 2001.

Schmitz, "Instrumentation for Real-Time Dynamic Optical Tomography," undated, SUNY Downstate Medical Center Brooklyn, NY, Nov. 2, 2001.

Smolinska and Dawidowicz, "Extraction of common or different part from optical images," Institute of Physics, Warsaw Technical University, 22-223 Dec. 13, 1983.

Gao X. et al., "Tunable focal depth of an apodized focusing optical system," Optical Engineering 44(6), 063001, Jun. 1-9, 2005.

Micro*color; RGB Tunable Filters for High-Resolution Color Imaging, Brochure, Cambridge Research & Instrumentation Inc. Oct. 2006.

(56) References Cited

OTHER PUBLICATIONS

Miao Q, Rahn J, Bryant R, et al.,"Multimodal three-dimensional imaging with isotropic high resolution using optical projection tomography." Proc SPIE. 2009;7262.

Miao Q, Hawthorne B, Meyer M, et al., "Dual modal three-dimensional imaging of single cell using optical projection tomography microscope." J Biomed Opt. 2009;14: 064035.

Neumann T, Meyer M, Patten F, et al., "Premalignant and malignant cells in sputum from lung cancer patients. Cancer Cytopathology." 2009;117:473-481.

Steinhauer D, Patten F, Meyer M, Nelson A., "Remote evaluation of 3D cell morphology for lung cancer screening and research." WCLC 2009 (sponsored by IASLC), J of Thor Oncol.

Neumann T, Yu J, Tourovskaia A, et al., "3D cytology in lung cancer: imaging of nuclear features and distribution of heterogeneous nuclear ribonucleoprotein A2/B1 (hnRNP A2/B1)." WCLC 2009 (sponsored by IASLC), J of Thor Oncol.

Meyer M, Patten F, Neumann T, et al., "The lung cell evaluation device (LuCED): early detection of lung cancer in sputum based on 3D morphology." WCLC 2009 (sponsored by IASLC), J of Thor Oncol.

Rahn J, Nelson A, Meyer M, Neumann T., "Cost effectiveness of automated 3D sputum cytology." WCLC 2009 (sponsored by IASLC), J of Thor Oncol.

Miao Q, Yu J, Meyer M, et al., "Dual-modal optical projection tomography microscopy for cancer diagnosis." Proc SPIE. 2010;7570.

Miao Q, Yu J, Rahn J, Seibel E., "Dual-mode optical projection tomography microscope using gold nanorods and hematoxylin-stained cancer cells." Optics Letters. 2010;35:1037-1039.

Miao Q, Hayenga J, Meyer M, Seibel E., "Resolution improvement in optical projection tomography by the focal scanning method." Optics Letters. 2010;35:3363-3365.

Miao Q, Hayenga J, Meyer M, et al., "High resolution optical projection tomographic microscopy for 3D tissue imaging." Proc. SPIE. 2011;7904.

Meyer M, Neumann T, Patten F, et al., "The LuCED test for detection of early lung cancer: a criterion to complete the test with high sensitivity." WCLC 2011 (sponsored by IASLC), J of Thor Oncol.

Willyard C., "Playing detective." Nature. 2012;491:64-65.

Dove A., "Digital imaging sees results." Life Science Technologies. 2012;336:1330-1332.

Miao Q, Reeves A, Patten F, Seibel E., "Multimodal 3D imaging of cells and tissue, bridging the gap between clinical and research microscopy. Annals of Biomedical Engineering." 2012;40:263-76.

Chou K, Miao Q, Coe R, Seibel E., "3D imaging of fine needle aspirates using optical projection tomographic microscopy." J Cytol & Histol. 2012:S2:001. doi:10.417212157-7099.

Meyer M, Patten F, Presley C, Neumann T, Nelson A., "Three-dimensional cellular morphometry: a new horizon for cytology and cancer detection." ASC 2012, J Am Soc Cytopathol. 2012;1:6-7.

Meyer M, Katdare R, Presley C, et al., "Lung cancer detection with LuCED, a novel test based on 3D cytometry of sputum cells." ASC 2012, J Am Soc Cytopathol. 2012;3:3-4.

Nelson A, Meyer M, Neumann T, et al., "Non-invasive detection of lung cancer from cells in sputum using Cell-CT™." WCLC 2013 (sponsored by IASLC), J of Thor Oncol.

Miao Q, Hu V, Seibel E., "Tissue imaging using optical projection tomographic microscopy." Proc. SPIE. 2014;9041.

Meyer M, Hayenga J, Neumann T, et al., "The Cell-CT 3-dimensional cell imaging technology platform enables the Detection of lung cancer using the noninvasive LuCED sputum test." Cancer Cytopathology. 2015;123:512-523.

Wilbur D, Meye M, Presley C, et al., "Automated 3-Dimensional morphologic analysis of sputum specimens for lung cancer detection: performance characteristics support use in lung cancer screening." Cancer Cytopathology. 2015;123:548-556.

Meyer M, Presley C, Wilbur D, et al., "Blinded evaluation of the LuCED test to detect early stage lung cancer." WCLC 2015 (sponsored by IASLC), J of Thor Oncol.

\* cited by examiner

SYSTEM AND METHOD FOR AUTOMATED DETECTION AND MONITORING OF DYSPLASIA AND ADMINISTRATION OF IMMUNOTHERAPY AND CHEMOTHERAPY

TECHNICAL FIELD

The present invention relates to optical tomography on a cellular and sub-cellular scale. More particularly, the invention relates to a system and method for determining dysplasia in a sample analyzed by an optical tomography system adapted for detection of dysplastic cells and consequently administering immunomodulating agents and/or other cancer chemoprevention pharmaceuticals to a subject to reduce dysplasia and lower the risk of lung cancer.

BACKGROUND

Lung cancer is the second most prevalent cancer in the United States and is the most lethal. Over 31 million patients in the United States (US) are at high risk for the development of lung cancer, primarily due to age, smoking history, and pollution and other factors including radon exposure, family history of lung cancer, etc. Approximately 160,000 US patients die of lung cancer each year. At the time of this writing, lung cancer can only be cured with surgery when detected in early stages, mainly stage I and II. However, lung cancer is known to be preceded by pre-cancerous conditions presenting as dysplastic cells. The detection of such pre-cancerous conditions can trigger preventative treatment that can reduce the risk of contracting lung cancer.

In one significant advance in the fight against lung cancer, U.S. Pat. No. 8,623,917, entitled "Uses of Prostacyclin Analogs," issued Jan. 7, 2014 to Keith et al. discloses a method for reducing a risk of developing lung cancer in a human former smoker. U.S. Pat. No. 8,623,917 (the Keith patent) is incorporated herein by reference. The method taught in the Keith patent comprises administering a therapeutically effective amount of prostacyclin analog comprising iloprost to the former smoker such that the risk of developing lung cancer in the former smoker is decreased by at least 10% relative to a control group with similar risk factors. Another aspect of the invention provides a method for reducing the risk of developing advanced premalignant dysplasia in a subject. While the Keith invention is an important development in the area of lung cancer prevention, there are significant difficulties in implementing this therapeutic method.

In a related published trial with a trial sample size of 152 subjects, participants were block randomized based on smoking status (current vs. former) and study center. The randomization sequence was generated prior to trial initiation and stored in a password-protected spreadsheet accessible only to the trial biostatistician and study administrator. Subjects were randomized only after confirmation of eligibility, and blinding was maintained throughout the trial. Following randomization, subjects were started on either iloprost or placebo at an initial dose of 1 tablet BID (50 μg iloprost clathrate per tablet). The subjects had a monthly clinical evaluation and if well tolerated, iloprost or placebo was dose escalated by 1 tablet monthly to a maximum dose of 3 tablets BID. Following 6 months of treatment, a second bronchoscopy was carried out with repeat biopsies at all of the baseline sites. Adverse events were monitored and reported twice yearly to an independent data and safety monitoring board (DSMB). A final clinical visit occurred 1 month after completing the trial and subjects are currently undergoing passive follow-up (i.e., yearly questionnaires). The trial involved 7 clinical centers (listed in the Appendix) funded by the National Cancer Institute as the Lung Cancer Biomarkers and Chemoprevention Consortium and individual site SPORE grants. The institutional review boards at each study center approved the study protocol. This trial was listed and registered on ClinicalTrials.gov (Identifier: NCT00084409). Bayer-Schering Pharma AG (Berlin) provided the study medication and placebo tablets (Keith et al., Cancer Prev Res (Phila). 2011 June; 4(6): 793-802. doi: 10.1158/1940-6207.CAPR-11-0057).

One significant obstacle to implementing the course of treatment taught in the Keith patent is identifying subjects with dysplasia who would most benefit from the administration of an immunomodulating agent such as iloprost. Iloprost has been suggested to possess anti-inflammatory and immunomodulating actions and it is widely used as a vasodilatator in systemic sclerosis (SSc). In one study the effect of iloprost on immune response in SSc patients was evaluated. Results demonstrated that Iloprost reduces T cell and TNF alpha production both in vivo and in vitro. It reduces T regulatory cells number, but increases their activity after immune stimulation. It increases serum IL-2 and this increase persists 28 days after the last infusion, also RANKL was increased both in vivo and in vitro. No effect on IFN gamma production was observed. These results suggest that iloprost has anti-inflammatory and immuno-modulating effects, reducing TNF alpha production by T cells and the number of T regulatory cells and increasing IL-2 and RANKL. (D'Amelio et al: Iloprost modulates the immune response in systemic sclerosis. BMC Immunology 2010 11:62.)

While patients with lung dysplasia may have elevated risk of lung cancer, they generally have no symptoms and are unaware of their condition. Currently, the most reliable technique for identifying dysplasia in a patient, broncho-scopic examination, requires anesthesia or sedation. Bron-choscopic examination of the lung typically includes several biopsies from both lungs, that is, an invasive procedure followed by pathology analysis. As a result, to date the class of patients proven to benefit from the iloprost treatment is limited to former smokers because, as a class, they are at high risk for lung cancer and it has been shown that the treatment would benefit former smokers as a class even without further testing for dysplasia. However, a chemopreventive drug would not be prescribed in the absence of a diagnostic test for dysplasia.

Furthermore, certain non-smokers may also have an unacceptably high incidence of lung cancer due to factors such as exposure to radon gas, coal dust, chemicals and other causes, both known and unknown. And former smokers who do not exhibit dysplasia may not be receiving any benefit from treatment with the drug. Therefore, a non-invasive test for reliably detecting dysplastic cells is urgently needed in order to identify subjects at risk of developing lung cancer, whether smokers, former smokers or non-smokers.

Another study is in continuing clinical trials as of April 2016, to determine whether calcitriol may prevent lung cancer in patients with metaplasia or dysplasia of the lungs. The purpose of this clinical trial is studying the side effects and best dose of calcitriol in preventing lung cancer in current smokers and former smokers at high risk of lung cancer. The study is being conducted by Roswell Park Cancer Institute in collaboration with the National Cancer Institute (NCI). The primary objectives of the study are to establish the safety of calcitriol in patients at high risk of lung cancer. To determine the dose-limiting toxicities of calcitriol in these patients.

In related developments, advances in 3D imaging of biological cells using optical tomography have been deployed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-Projection Formation for Optical Tomography," (Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein, an early lung cancer detection technology has been fully developed and commercialized by VisionGate, Inc., Phoenix, Ariz. to provide measurement advantages that have demonstrated a great improvement in the operating characteristics of conventional morphologic cytology analyses.

Processing in such an optical tomography system begins with specimen collection and preparation. For diagnostic applications in lung disease, patient sputum can be collected non-invasively in a clinic or at home. At the clinical lab, the sputum is processed to remove non-diagnostic material, fixed and then stained. Stained specimens are then mixed with an optical gel, and the suspension is injected into a microcapillary tube. Images of objects, such as cells, in the specimen are collected while the cells are rotated around 360-degrees relative to the image collection optics in an optical tomography system. The resultant images comprise a set of extended depth of field images from differing perspectives called "pseudo-projection images." The set of pseudo-projection images can be mathematically reconstructed using backprojection and filtering techniques to yield a 3D reconstruction of a cell of interest. Having isometric or roughly equal resolution in all three dimensions is an advantage in 3D tomographic cell imaging, especially for quantitative feature measurements and image analysis.

The 3D reconstructed digital image then remains available for analysis in order to enable the quantification through the measurement of sub-cellular structures, molecules or molecular probes of interest. An object such as a biological cell may be stained or labeled with at least one absorbing contrast agent or tagged molecular probe, and the measured amount and structure of this biomarker may yield important information about the disease state of the cell, including, but not limited to, various cancers such as lung, breast, prostate, cervical, stomach and pancreatic cancers, and various stages if dysplasia.

However, until the disclosure herein, there was no reliable method for employing optical tomography for identifying pre-cancerous conditions like dysplasia. By providing here a method and system for identifying dysplastic cells, a patient can be treated with an immunomodulating agent such as iloprost in order to lower the risk of developing lung cancer in a more focused class of patients at risk than alternatively only administering treatment to patients who are at extremely high risk of lung cancer due to age and exposure to carcinogens.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method of treating a malignancy in a human subject by analyzing pseudo-projection images of cells obtained from a sputum specimen obtained from a subject is provided. A biological specimen classifier identifies cells from the sputum specimen as normal or abnormal. If abnormal cells are detected, then the abnormal cells are further classified as dysplastic or cancerous. If the cells are classified as dysplastic, then an immunomodulating agent is administered to the subject over a predetermined time period designed to achieve a therapeutic dosage.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
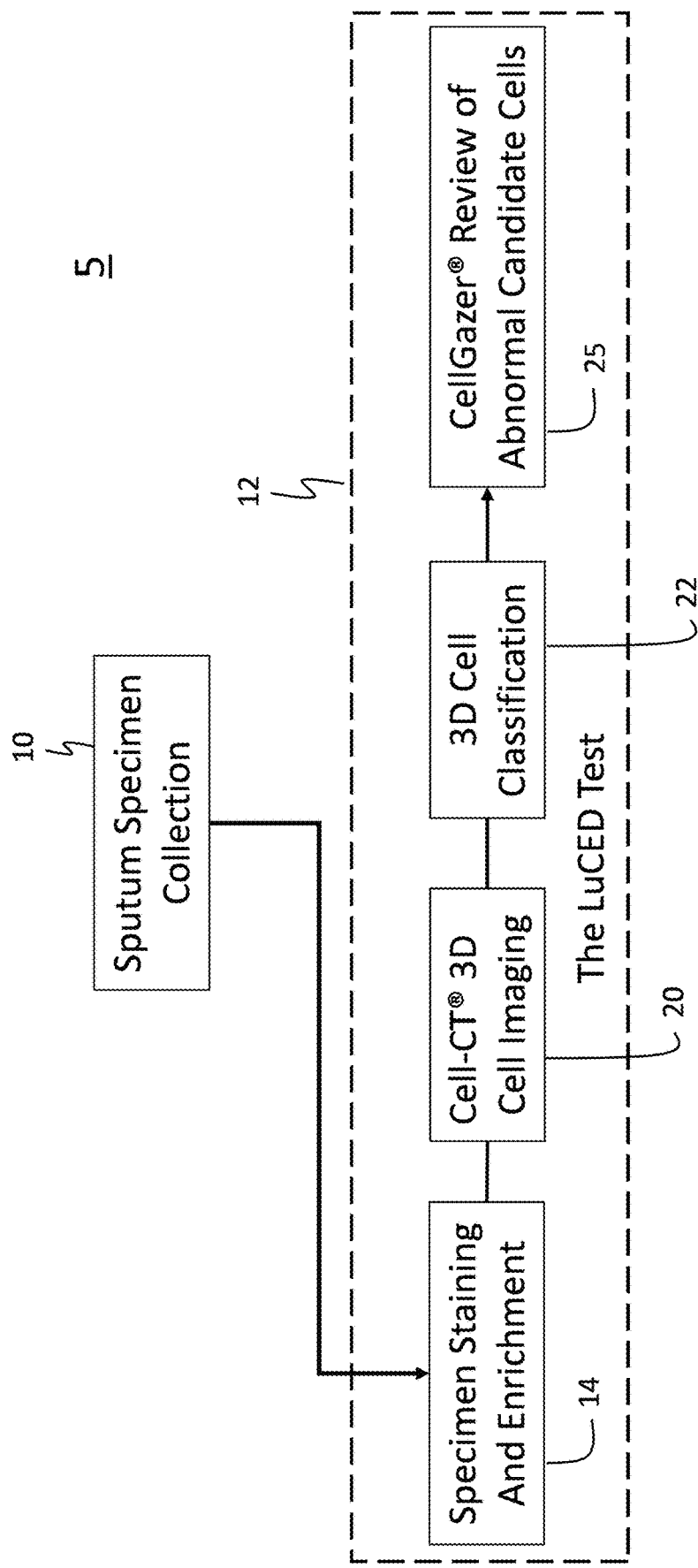
FIG. 1 schematically shows a functional overview of a lung cancer test for analysis of a sputum sample.

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION OF THE PREFERRED EMBODIMENTS

The following disclosure describes a method of treating a malignancy in a human subject by analyzing 3D images of cells obtained from a sputum specimen followed by treatment with immunotherapy when indicated. Several features of methods and systems in accordance with example embodiments are set forth and described in the figures. It will be appreciated that methods and systems in accordance with other example embodiments can include additional procedures or features different than those shown in the figures. Example embodiments are described herein with respect to an optical tomography cell imaging system. However, it will be understood that these examples are for the purpose of illustrating the principles, and that the invention is not so limited.

The present invention provides an early lung dysplasia and cancer detection system using specimens including patient sputum which is processed by an optical tomography system that produces isometric, sub-micron resolution 3D cell images that are then processed by automated feature extraction and classification algorithms to identify abnormal cells in sputum with high accuracy. Since abnormal cells are rare in sputum and non-diagnostic contaminants are plentiful, only a system capable of cell detection with high sensitivity and very high specificity can manage the lung cancer detection in sputum in an efficient way while assuring specimen adequacy.

There are many potential uses of the presently disclosed optical tomography system; the most advantageous being in specimens that have low yields of neoplastic cells or in which the abnormal cells are difficult to recognize when compared to the background of non-neoplastic cells. Examples include the detection of dysplastic cells, circulating tumor cells in blood and neoplastic cells in sputum in cases of early or peripheral lung cancer.

DEFINITIONS

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Adequacy" refers to the content of the specimen and defines a limit for target cells to determine if a sufficient cellular pellet has been analyzed.

"Calcitriol" as used herein is a synthetic (man-made) active form of vitamin D3 (cholecalciferol).

"Capillary tube" has its generally accepted meaning and is intended to include transparent microcapillary tubes and equivalent items with an inside diameter generally of 500 microns or less, but larger diameters could be used.

"Cell" means biological cell such as a human, mammal or animal cell.

"Cell-CT® platform" refers to an optical tomography system manufactured by VisionGate, Inc. of Phoenix, Ariz. incorporating teachings of the Nelson and Fauver patents referenced herein above and improvements of those teachings.

"CellGazer" a software-based utility to foster review of 2D and 3D images of cells rendered by the Cell-CT. The result of cell review is a detailed differential diagnosis of the cell type that then determines the final result of a case processed, for example by the LuCED test.

"Chimeric antigen receptors (CARs)" as used herein mean Artificial T cell receptors (also known as chimeric T cell receptors, or chimeric immunoreceptors) are engineered receptors, which graft an arbitrary specificity onto an immune effector cell.

"CIS" as used herein has its generally accepted meaning of Carcinoma in situ, also known as in situ neoplasm.

"Depth of field" is the length along the optical axis within which the focal plane may be shifted before an unacceptable image blur for a specified feature is produced.

"Enrichment" refers to the process of extracting target cells from a raw specimen. The process yields an enriched pellet whose cells can then be more efficiently imaged on the Cell-CT system.

"Immunotherapy" as used herein applies to the field of oncology and means a method of ameliorating, treating, or preventing a malignancy in a human subject wherein the steps of the method assist or boost the immune system in eradicating cancerous cells, including the administration of cells, antibodies, proteins, or nucleic acids that invoke an active (or achieve a passive) immune response to destroy cancerous cells. It also encompasses the co-administration of biological adjuvants (e.g., interleukins, cytokines, *Bacillus* Comette-Guerin, monophosphoryl lipid A, etc.) in combination with conventional therapies for treating cancer such as chemotherapy, radiation, or surgery, administering any vaccine that works by activating the immune system to prevent or destroy cancer cell growth and in vivo, ex vivo, and adoptive immunotherapies, including those using autologous and/or heterologous cells or immortalized cell lines.

"Iloprost" as used herein is an immunomodulating agent which comprises a synthetic analogue of prostacyclin $PGI_2$.

"LuCED® test" refers to an early lung cancer detection test employing the Cell-CT® platform as developed by VisionGate, Inc. of Phoenix, Ariz. incorporating the teachings of the Nelson and Fauver patents referenced hereinabove and improvements of those teachings.

"The LuCED® process" refers to the mechanism of 3D cell reconstruction, classification to find abnormal cells, and pathology confirmation.

"LDCT" means low dose computer tomography (CT) radiographic scanning.

"Object" means an individual cell, human cell, mammal cell, item, thing or other entity.

"Pseudo-projection" includes a single image representing a sampled volume of extent larger than the native depth of field of the optics where pseudo-projection image thus formed include an integration of a range of focal plane images from a fixed viewpoint. The concept of a pseudo-projection is taught in Fauver '945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"ROC" has its generally accepted meaning of Receiver Operator Characteristic.

"Sample" means a finished cellular preparation that is ready for analysis, including all or part of an aliquot or specimen.

"Subject" as used herein means a human patient.

"Target Cell" refers to a cell from a specimen whose characterization or enumeration is especially desired. For example, in the LuCED test, the target cells are the normal bronchial epithelial cells. A minimum number of these must be enumerated during the test in order for a specimen to be considered as adequate.

"Threshold" as used in the context of image processing includes a decision boundary value for any measurable characteristic of a feature. Thresholds may be predetermined or set according to instrument specifications, acceptable error rates, statistics, or other criteria according to accepted pattern recognition principles.

"TNM stage" is used herein in its generally accepted sense within the context of lung cancer and means tumor, node, metastasis (TNM) staging as defined by medical associations as, for example, by The International Association for the Study of Lung Cancer (IASLC).

Vorinostat also known as suberanilohydroxamic acid is used in its usual meaning as a histone de-acetylace (HDAC) inhibitor used in Barrett's esophagus.

"Voxel" as used in the context of image processing is a volume element on a 3D grid.

Overview

Referring to FIG. 1, a functional overview of a lung dysplasia and cancer test system for analysis of a sputum sample is schematically shown. The test system 5 includes apparatus and methods for sputum specimen collection 10 followed by a test for early lung cancer detection 12 such as, for example, the LuCED® test. The early lung cancer test 12 further includes an apparatus and methods for specimen staining and enrichment 14, 3D cell imaging 20, 3D cell classification 22 and clinician review of abnormal candidate cells 25.

Sputum collection is typically done through spontaneous coughs in the patient's home or through induction in a clinic. Sputum is processed to remove contaminants and non-bronchial epithelial cells as, for example, by de-bulking the white cells and oral squamous cells. The enriched specimen is processed on the Cell-CT® platform that images cells digitally in true 3D with isometric, sub-micron resolution as disclosed, for example in Nelson and Fauver referenced above. The bio-signatures associated with cancer are measured on the 3D cell images and combined into a score that is used to identify those few cells that have cancer characteristics. These cells are then optionally displayed for manual cytologist review using a review station such as a CellGazer™ review station as developed by VisionGate, Inc., Phoenix, Ariz. The review station provides visual displays allowing a cytologist to view cell images in 2D and 3D to establish a definitive normal or abnormal status for specific cell candidates. Three-dimensional (3D) cell classification 22 may be carried out using techniques as disclosed herein below.

The cell imaging system 20 includes a process implemented through computer software executed, for example, by a personal computer interfacing with opto-mechanical devices to correct for motion arising during image capture. Most cell images emerge from filtered back-projection in a well-reconstructed way. This algorithm identifies cells that were poorly reconstructed so they can be rejected from further processing. One example of a method for detecting poor quality reconstructions is taught by Meyer et al. in U.S. Pat. No. 8,155,420, issued Apr. 10, 2012 and entitled "System and Method for Detecting Poor Quality in 3D Reconstructions," the disclosure of which is incorporated herein by reference.

Earlier attempts at the development of a lung cancer-screening program were based on sputum cytology which showed an insufficient sensitivity to disease detection by human eye (about 60% on average) but with very good specificity (Schreiber and McCrory (2003) Chest 123 (1 Supplement): 115). This experience led some to conclude that sputum is not valuable for detection of lung cancer. A careful analysis involving sputum embedded in paraffin blocks (Böcking A, Biesterfeld S, Chatelain R, Gien-Gerlach G, Esser E., Diagnosis of bronchial carcinoma on sections of paraffin-embedded sputum. Sensitivity and specificity of an alternative to routine cytology. Acta Cytol. 1992; 36(1):37-47) showed that the specimen actually contains abnormal cells in 86% or more of cancer patients. Collection by morning coughs over three successive days yielded optimal results. A further analysis showed that abnormal cells are present in sputum stratified by all relevant clinical factors, including tumor histologic type, size, stage and location (Neumann T, Meyer M, Patten F, Johnson F, Erozan Y, Frable J, et al. Premalignant and Malignant Cells in Sputum from Lung Cancer Patients. Cancer Cytopathology, 2009; 117(6):473-481). Based on these specimen characteristics, the presently disclosed lung cancer detection test employs spontaneous cough sputum. Initial evaluations have shown satisfactory results using sputum fixation by either Cytoyt (Hologic, Marlborough, Mass.) or the well-known Saccomanno's method. The question of specimen adequacy is also important for sputum cytology. Attempts at increasing the volume of the sputum expectorate have met with varied success. Sputum induction increases production of phlegm to help achieve an overall adequate sample.

Examples of Sputum Enrichment and Preparation

In one example of a lung cancer detection test adapted for detection of dysplasia, sputum specimens undergo three stages of processing prior to analysis: 1) sputum cell isolation and cryopreservation; 2) enrichment by fluorescence activated cell sorting (FACS); and 3) embedding of enriched cells into optical oil that is index-matched to the optical components of the optical tomography imaging system.

Cryopreservation and FACS Enrichment (FACS being One Example)

Sputum is treated with the mucolytic agent dithiothreitol (DTT) (Fisher Scientific, Waltham, Mass.). In one example, for longer term storage, the specimen was filtered through a 41 µm nylon net and kept at −80° C. in 15% dimethyl sulfoxide (DMSO) (Fisher Scientific, Waltham, Mass.). After filtration, an aliquot of up to 100 µL of the preserved specimen is removed for lung cancer detection test analysis. First, sputum cells were stained with hematoxylin (Electron Microscopy Sciences, Hatfield, Pa.) for downstream lung cancer detection test imaging. Cells were then treated with an antibody cocktail containing fluorescent conjugates chosen to both enrich for bronchial epithelial cells and to deplete contaminating inflammatory cells (neutrophils and macrophages). An anti-cytokeratin-FITC conjugate cocktail (Cell Signaling, Danvers, Mass.) targets cytokeratins expressed in both normal and malignant epithelial cells. An Anti-CD45-APC conjugate (Mylteni, Bergisch Gladbach, Germany)

targets inflammatory cells for negative selection. Cells are also stained with DAPI (Life Technologies, Grand Island, N.Y.) prior to cell sorting. For FACS enrichment, a DAPI-positive mother gate was created to exclude doublet cells and debris, followed by exclusion of high side-scatter events, which are primarily oral squamous cells. Subsequently, a cytokeratin-high (High FITC) and CD45-Low (Low APC) daughter gate is drawn. The population of cells in this daughter gate were the enriched target epithelial cells sorted for a more efficient and downstream lung cancer detection test analysis using an optical tomography system such as the Cell-CT® optical tomography system.

Embedding of Enriched Cells

Following FACS enrichment (or any other process of enrichment), cells are dehydrated in ethanol followed by suspension in xylene. The cells are then transferred to and embedded in a suitable volume of the optical medium. The optical medium is a viscous oil with matching refractive index for the optical tomography system. Once embedded, cells are injected into a disposable cartridge for imaging on the optical tomography system.

Figure 2:
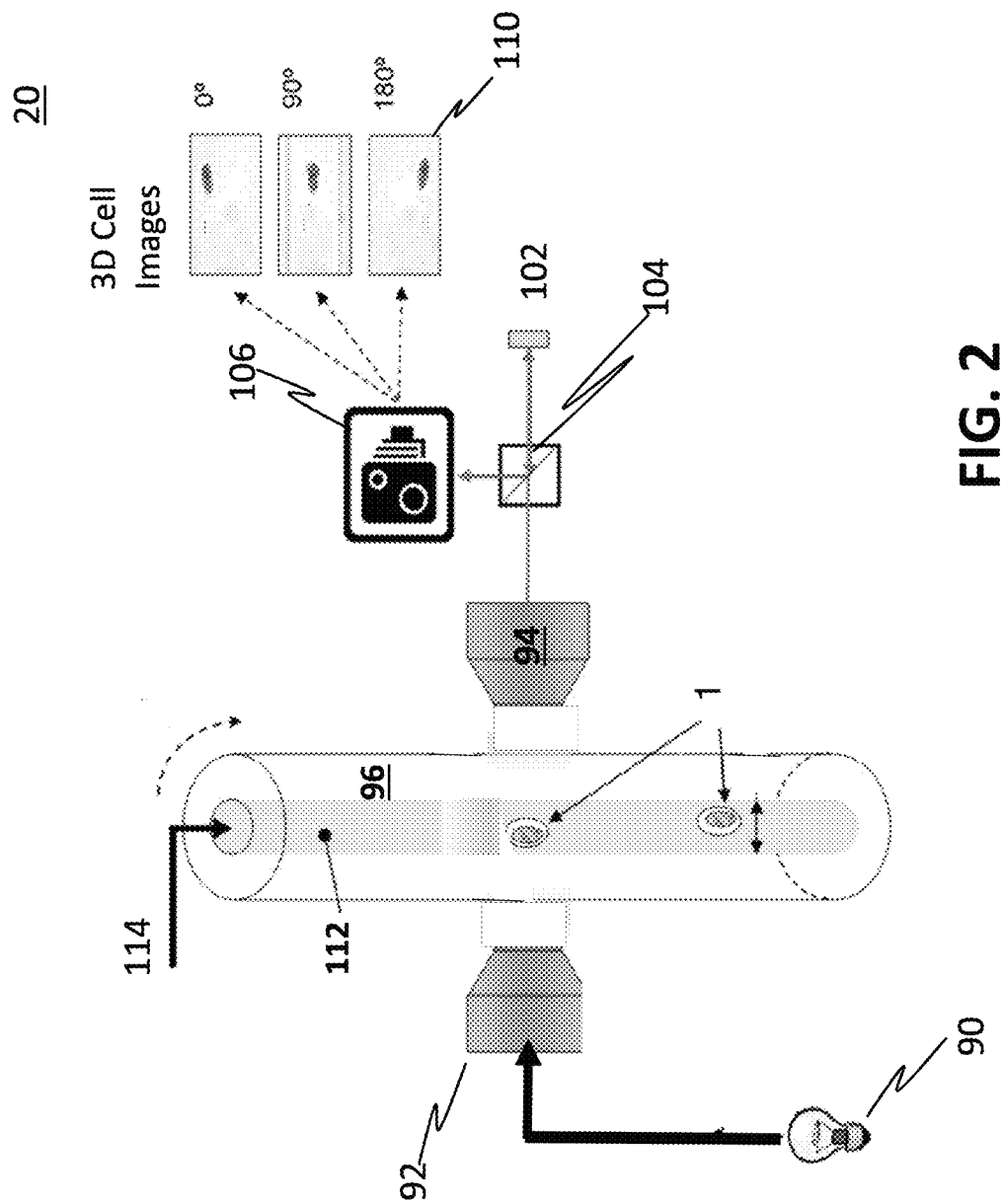
FIG. 2 schematically shows basic system components of a 3D optical tomography imaging system used in a lung cancer test system.

Referring now to FIG. 2, basic system components of a 3D optical tomography imaging system used in a lung cancer test system. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high speed camera produces a plurality of pseudo-projection images 110. A set of pseudo-projection images for numerous axial tube rotation positions is produced for each object.

Although the test system is not limited to any one contrast method, in one example the lung cancer detection test specifically targets cell morphology based on the traditionally used hematoxylin stain. In the lung cancer detection test application, the optical tomography system computes 3D cell images with equal resolution in all dimensions (i.e. isotropic resolution) allowing measurements to be independent of orientation. Further, eliminating the focal plane ambiguity and view orientation dependencies typical of conventional microscopy provides information content to automatically recognize a broad spectrum of cell types, and unambiguously identify rare abnormal cells in a predominantly normal cell population. The optical tomography system output identifies about 0.5% of all cells as abnormal candidates to be verified using the CellGazer™ (VisionGate, Phoenix, Ariz.) workstation, an imaging software tool that allows human review of images free of focal plane and orientation ambiguity.

Optical tomography system imaging is performed on a small-volume liquid suspension. For lung cancer detection testing these cells are from the enriched epithelial cell population noted above. Because the optical tomography system can separate closely coincident objects, a narrowly focused core of single file cell flow, although a requirement in standard flow cytometry, is unnecessary.

The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, "Optical Tomography System with High-Speed Scanner," which is also incorporated herein by reference. In operation stained nuclei of a biological cell 1 are suspended an optical media 112 and injected into a capillary tube 96 having, for example, a 62 µm inner diameter. The capillary system has been designed to be disposable, thus eliminating the possibility of cross-contamination between specimens. Pressure 114 is applied to the fluid moves objects 1 into position for imaging, before 3D data is collected as the tube rotates. A mirror 102 is actuated to sweep the plane of focus through the object, and the image is integrated by the camera to create a pseudo-projection from each single perspective. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses. A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell may be rotated to allow capture of a set of 500 pseudo-projections is taken as the capillary rotates through 360 degrees. Because the cells are suspended in a fluid medium, they are prone to a small amount of movement while pseudo-projection images 110 are collected.

Cell images in the pseudo-projections, therefore, must be registered to a common center so that the cell features reinforce one another during the reconstruction. U.S. Pat. No. 7,835,561, entitled "Method for Image Processing and Reconstruction of Images for Optical Tomography," discloses error correction techniques for pseudo-projections. U.S. Pat. No. 7,835,561, is hereby incorporated by reference. The set of corrected pseudo-projections is processed using a filtered back-projection algorithm, similar to that in use in conventional X-ray CT, to compute the tomographic 3D cell reconstruction. Pseudo-projections images 110 taken at three angular positions: 0 g, 90 g and 180 g are shown. Illumination is provided by a light source 90 at 585 nm wavelength to optimize image contrast based on the hematoxylin absorption spectrum. In the reconstruction, 3D pixels or voxels are cubic, with a size of 70 nm in each dimension. Reconstruction volumes vary in size, as the image collection volume is cropped around the object. Typically, volumes are approximately 200-300 pixels on the side.

Figure 3:
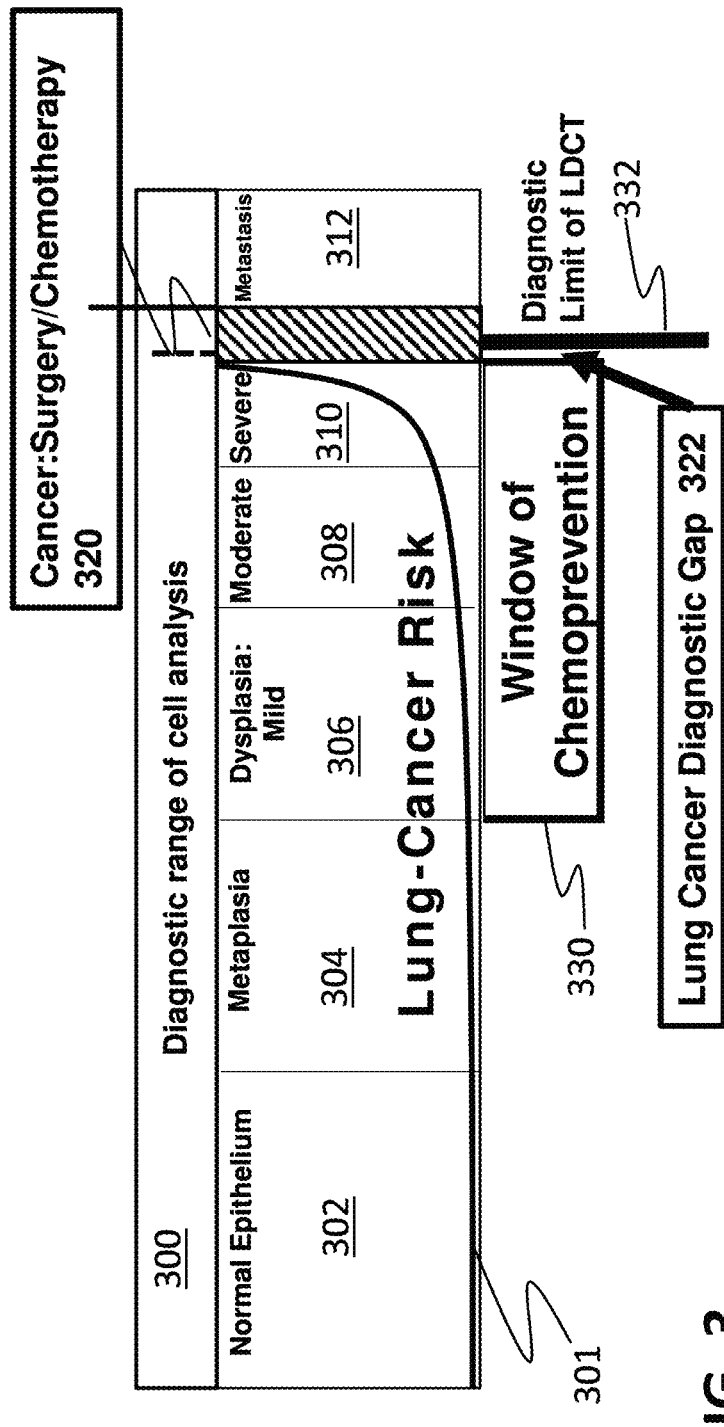
FIG. 3 graphically illustrates a correlation of stages of pre-malignancy with lung cancer risk.

Referring now to FIG. 3, a correlation of stages of pre-malignancy with lung cancer risk is graphically illustrated. Chart 300 illustrates how stages of pre-malignancy correlate with lung cancer risk over a diagnostic range of cell analysis. Curve 301 represents a relative measure of risk which increase from left to right. A first stage 302 represents a diagnosis of a normal epithelium. A second stage 304 represents a diagnosis of metaplasia. A third stage 306 represents a diagnosis of mild dysplasia. A fourth stage 308 represents moderate dysplasia. A fifth stage 310 represents severe dysplasia. A sixth stage 320 represents a diagnosis of cancer requiring surgery and/or chemotherapy. A final stage 312 represents metastasis. A window of chemoprevention 322 exists before the cancer stage 320 and during any of the dysplasia stages. For comparison, a broad line 332 represents the diagnostic limit of LDCT.

Figure 4:
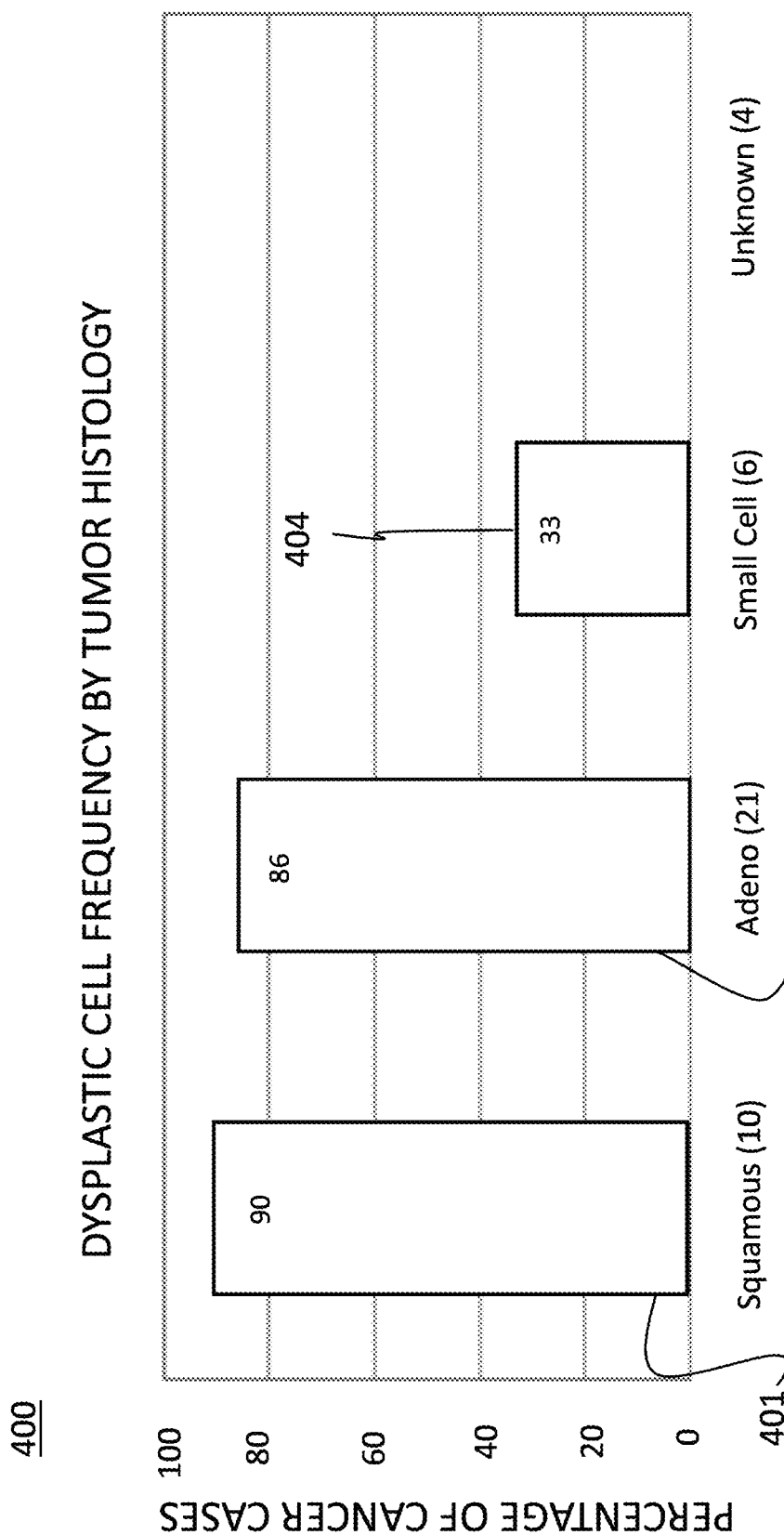
FIG. 4 plots the percentage of sputum samples where dysplastic cells were found versus the tumor histology for cancer cases.

Referring now to FIG. 4, the percentage of sputum samples where dysplastic cells were found versus the tumor stage for cancer cases is plotted. In the plot 400 the percentage of cancer cases with dysplastic cells found through the LuCED process is broken down by histology. Bar 401 represents 90% detection of dysplastic cells for squamous cell cancer out of a population of 10 known cells. Bar 402 represents 86% detection of dysplastic cells for adeno carcinoma out of a population of 21 known cells. Bar 404 represents 33% detection of dysplastic cells for small cell carcinoma out of a population of 6 known cells.

Figure 5:
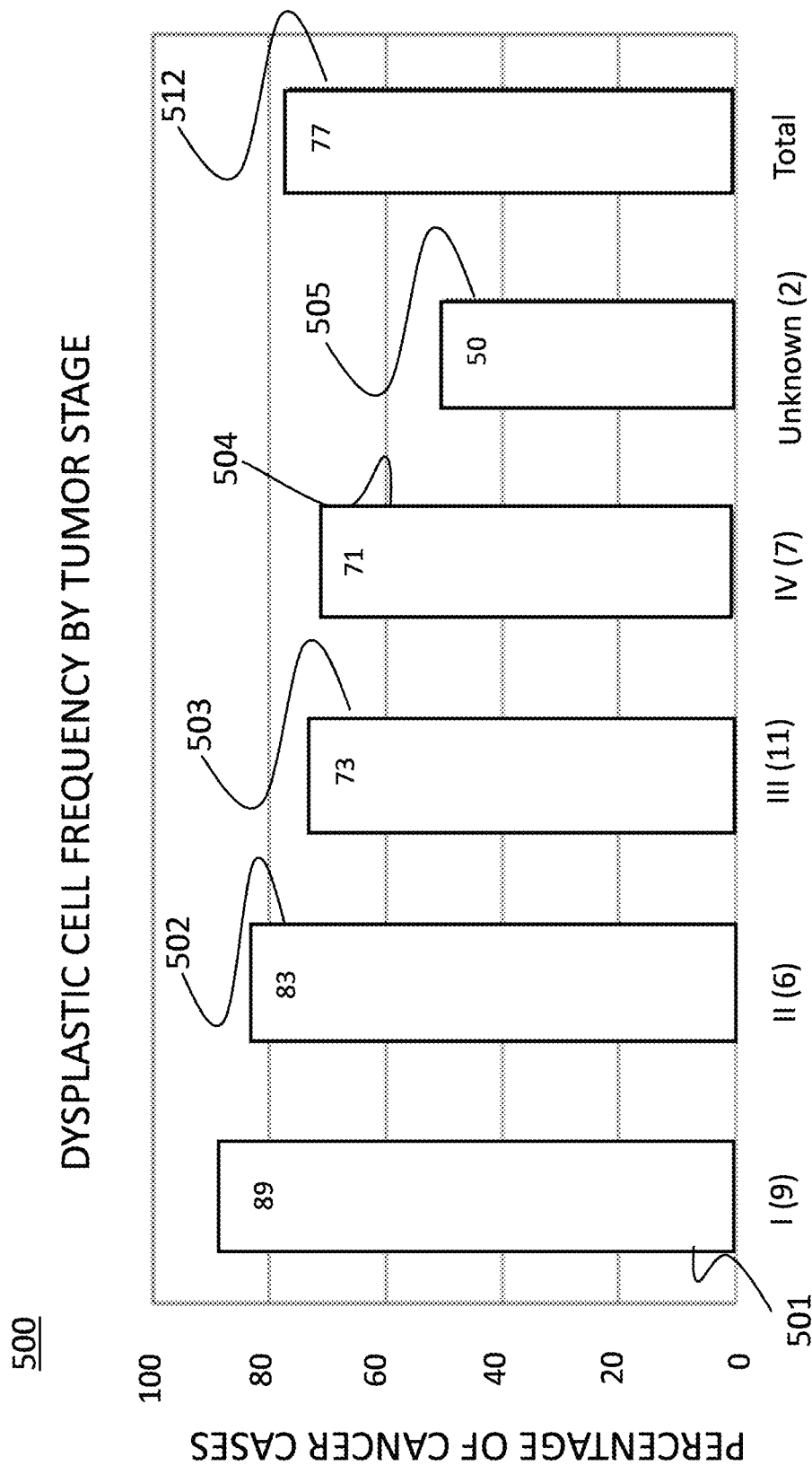
FIG. 5 plots the percentage of sputum samples where dysplastic cells were found versus the tumor stage for cancer cases.
Figure 6:
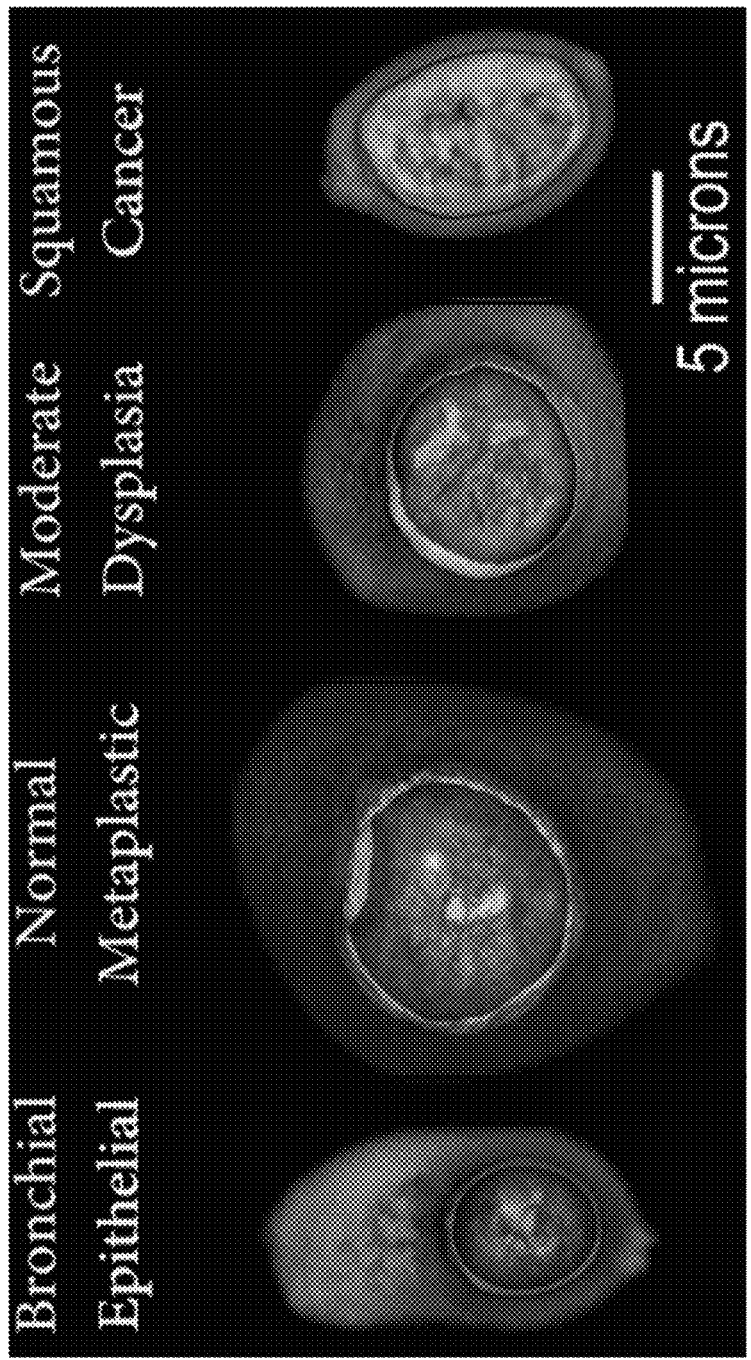
FIG. 6A-FIG. 6D show views of cell 3D reconstruction identified as glandular atypia, moderate/severe dysplasia and cancer cells.

Referring now to FIG. 5, the percentage of sputum samples where dysplastic cells were found versus the tumor histology for cancer cases is plotted. Plot 500 provides an assessment of the percentage of cancer cases with dysplastic cells found through the LuCED process sub-divided by the tumor stage. Bar 501 represents an 89% detection rate for dysplastic cells out of a population of 9 stage I cancer cells. Bar 502 represents an 83% detection rate for dysplastic cells out of a population of 6 stage II cancer cells. Bar 503 represents a 73% detection rate for dysplastic cells out of a population of 11 stage III cancer cells. Bar 504 represents a 71% detection rate for dysplastic cells out of a population of 7 stage IV cancer cells. Bar 505 represents a 50% detection rate for unknown cells out of a population of 2 unknowns. Bar 512 represents a 50% detection rate for dysplastic cells out of a population of 2 unknowns.

Referring now to FIG. 6A-FIG. 6D, views of sectioned, 3D cell images identified as glandular atypia, moderate/severe dysplasia and cancer cells are shown. The figures are scaled relative to 5 microns as shown. Each cell imaged is assigned a classification score as discussed herein with reference, for example, to FIG. 9. The final diagnosis of moderate dysplasia, atypical columnar cell, etc., is made by a pathologist who examines the cells forwarded for review by LuCED® testing.

Figure 7:
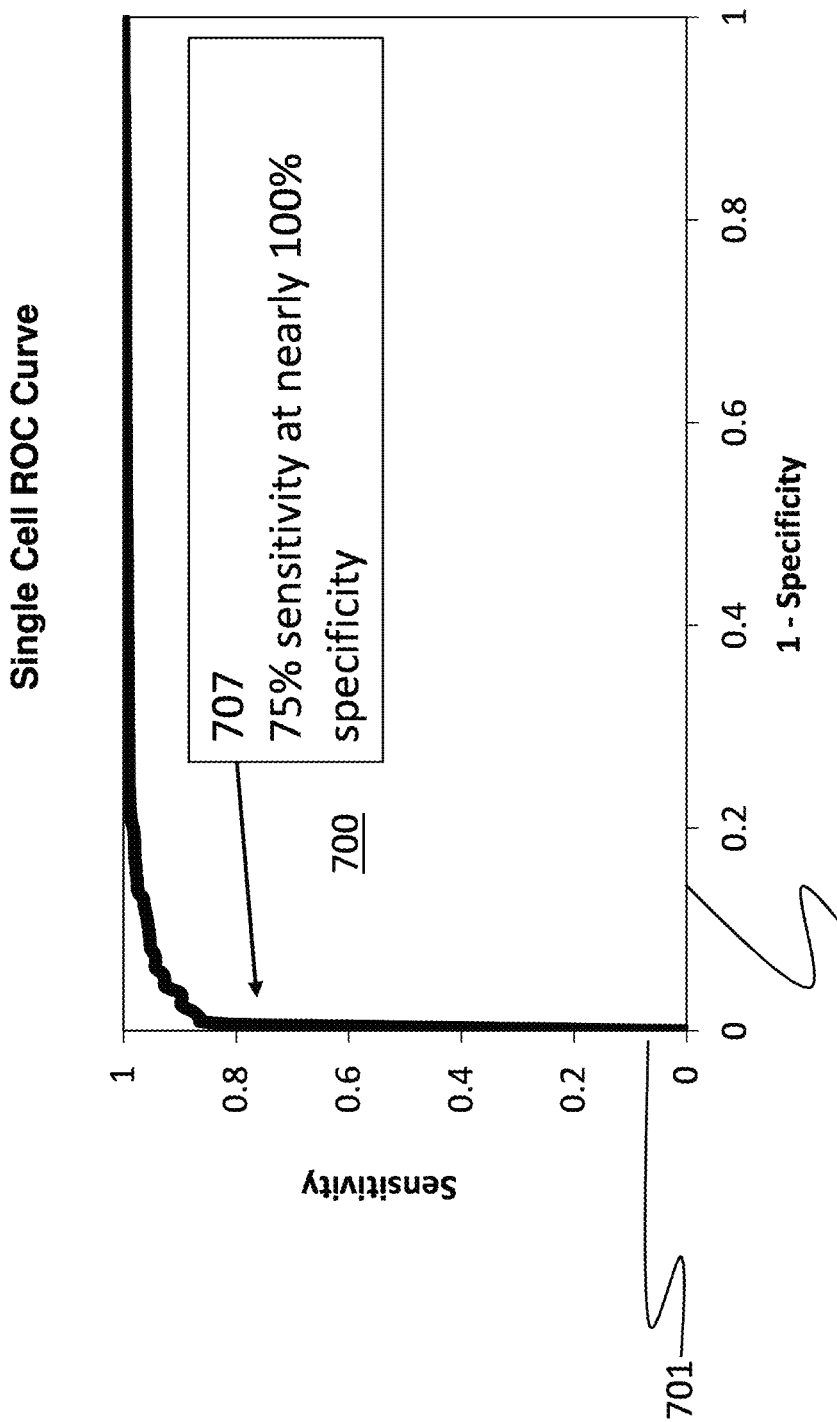
FIG. 7 shows an ROC curve of sensitivity vs. 1-specificity for a dysplastic cell classifier.

Referring now to FIG. 7 shows an ROC curve for a dysplastic cell classifier. ROC curve 700 is a plot of sensitivity to dysplastic cells on the vertical axis 701 against 1-specificity on the horizontal axis 703. Point 707 indicates a region where the dysplastic cell classifier performs with 75% sensitivity at nearly 100% specificity. The classifier was constructed using a data set including cells indicating an abnormal lung process consisting of moderate to severe dysplasia and some atypical cellular conditions. Training of the classifier was implemented using a set of about 150 known dysplastic cells and about 25,000 known normal cells. Accuracy is demonstrated by the single cell ROC curve 700 which shows near perfect detection of dysplastic cells. Classifier accuracy is often expressed as the area under the ROC curve (AROC). Perfect discrimination results when the AROC is 1. The LuCED AROC value is 0.991. For single cell detection, an operating point was selected that provides 75% sensitivity and 100% specificity. Cell classification relates to detection of the case as shown in the list below. For example, if one abnormal cell was encountered during LuCED analysis then the case detection probability would be 0.75, or 75%. If two abnormal cells were encountered by LuCED then the case detection probability would be $(1-(1-0.75)^2)=0.9375$ or nearly 94% case sensitivity, etc.

1 cell—75% case sensitivity,
2 cells—94% case sensitivity, and
3 cells—98% case sensitivity.

Cell Classification

Figure 8:
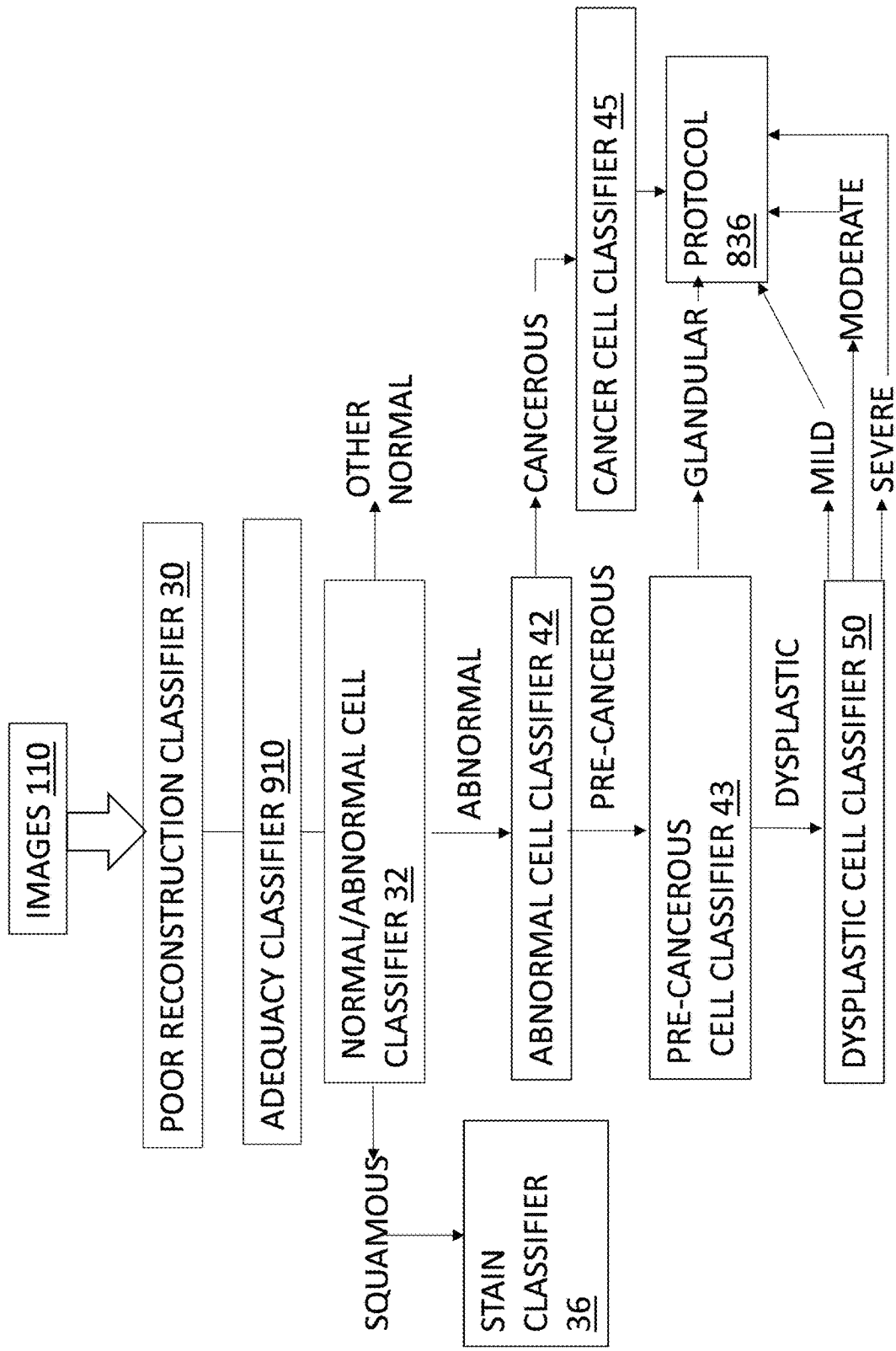
FIG. 8 schematically shows a functional block diagram of a cell classification system for analysis of a sputum sample for dysplasia and cancer.

Now referring to FIG. 8, several cell classification algorithms are included in the system for detection of dysplasia and other conditions. In one example, the classifiers include a classifier to detect poor reconstructions 30, an adequacy classifier 910, a normal/abnormal cell classifier 32, a stain classifier 36, an abnormal cell classifier 42, a pre-cancerous cell classifier 43, a cancer cell classifier 45 and a dysplastic cell classifier 50. The pre-cancerous cell classifier 43, cancer cell classifier 45 and dysplastic cell classifier 50 are coupled to provide classification data to a treatment protocol generator 836 (discussed in detail below). The classifiers used in the cytological detection system are trained as described below. In one useful example, the classifier to detect poor reconstructions 30 may be as described hereinabove with reference to Meyer et al. Prior to classification of the cell as normal or abnormal the specimen adequacy classifier 910 is applied. One such method for determining specimen adequacy is taught in detail in U.S. Pat. No. 9,594,072, to Meyer, et al., issued Mar. 14, 2017. U.S. Pat. No. 9,594,072 is incorporated herein by reference. In one example, classifiers for a normal cell gallery 32 identify normal cells to serve as a reference point for human identification of abnormal cells using a review station. Normal cell types may be subdivided into classes including normal squamous intermediate cells, and other normal cells including normal columnar epithelial cells, and normal macrophages.

The stain classifier 36 operates, for example, by processing cells identified as squamous intermediate cells in order to determine whether the cells are in the correct stain range for LuCED testing. The nucleus of a squamous intermediate cell has constant ploidy, making its overall integrated grey-scale optical density value an ideal feature that can be used to assess whether specimen staining is in the correct range for optimal absorption contrast. Average and median grey scale values may be computed for each nuclei and a running average maintained. The stable value for the average is the stain that may be used as normalization for the individual grey scale values of the nucleus under consideration.

The abnormal cell classifier 42 is generated by being trained to identify target cells having abnormal characteristics using classifier training methods described herein. These target cells (typically 0.5% of all cells processed) go on to be examined by a pathologist using the review station 25, such as a CellGazer™ workstation as developed by VisionGate, Inc. of Phoenix, Ariz. In certain embodiments target cells include abnormal squamous cells, adenocarcinoma cells, bronchioloalveolar carcinoma cells, abnormal neuroendocrine cells, small cell carcinoma cells, large cell carcinoma cells, lung columnar cells, tumor cells, neoplastic cells and bronchioloalveolar carcinoma cells and other cells and objects found in sputum. The abnormal cell classifier operates to identify cancerous and pre-cancerous cells.

Pre-cancerous cells are further analyzed by pre-cancerous cell classifier 43. The pre-cancerous classifier distinguishes between pre-cancerous cells of glandular origin vs. pre-cancerous of squamous origin (dysplasia). If the cells are dysplastic, they are further routed to the dysplastic cell classifier 50. The dysplastic cell classifier 50 is generated by being trained to identify target cells having characteristics using classifier training methods. As discussed hereinabove with reference to FIG. 7, the dysplastic classifier was trained using a set of about 150 known dysplastic cells and about 25,000 known normal cells. The dysplastic cell classifier 50 further identifies cells as exhibiting mild, moderate, or severe dysplasia.

Figure 9:
FIG. 9 schematically shows a functional block diagram of one example of a cancer cell classifier.

Referring now to FIG. 9, a functional block diagram of one example of a cancer cell classifier 45 for analysis of a sputum sample for dysplasia and cancer is schematically shown. The cancer cell classifier further classifies cells as adenocarcinoma, small cell carcinoma, or squamous carcinoma cells.

In order to promote better understanding of the system and method disclosed herein, an example of the system operation will now be described in detail. Treatment options are selected depending upon the classifications determined by the classifier algorithms from a sputum specimen as discussed above.

Figure 10:
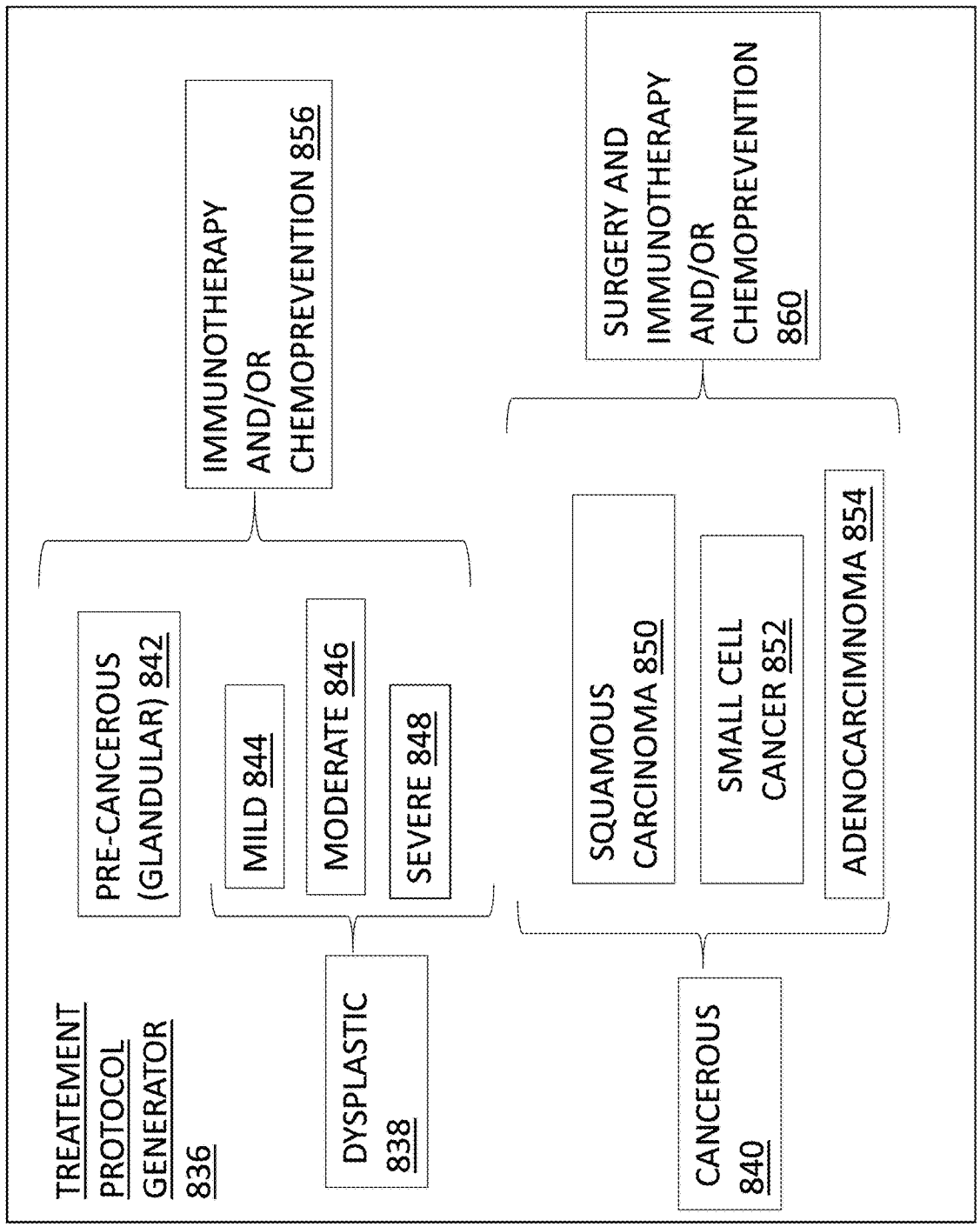
FIG. 10 schematically shows a high level functional block diagram of a treatment protocol generator.

Referring now to FIG. 10, a high level functional block diagram of a protocol generator is schematically shown. In operation, if abnormal cells are detected by the normal/abnormal cell classifier 32, then the abnormal cells are further classified by the abnormal cell classifier 42 as pre-cancerous 842 or cancerous 840. As described above, cells classified as cancerous 840 are further identified as adenocarcinoma 854, small cell carcinoma 852, or squamous carcinoma cells 850. A biopsy may be performed to verify suspicious lesions. If cancer is found as a result of the biopsy, then surgical procedures should be carried out to remove the cancer lesion or lesions coupled with immunotherapy and/or chemoprevention treatment 860.

If pre-cancerous cells are detected then the precancerous cell classifier 43 is operated to classify cells from the sputum sample as pre-cancerous cells of glandular origin 842, or dysplastic 838. If the cells are classified as pre-cancerous, then a cancer chemoprevention pharmaceutical 856 is administered to the subject over a predetermined time period. Subsequently, dysplastic cells are classified by the dysplastic cell classifier into mild-moderate dysplasia, moderate to severe dysplasia or severe dysplasia. If cells are classified as mild, moderate or severe dysplasia, then a cancer chemoprevention pharmaceutical 856 is administered to the subject over a predetermined time period. In the case where both pre-cancerous and cancer cells are discovered then the cancer status of any suspicious lesions is verified and, if cancer is found, then surgical procedures to are administered to remove the cancer lesion and an immunomodulation agent and/or a cancer chemoprevention pharmaceutical is administered to the subject over a predetermined time period. Useful cancer immunomodulating agents include a drug selected from the group consisting of a chimeric immunoreceptor, a prostacyclin analog, iloprost, a chimeric antigen receptor (CAR) for T-cells, Vorinostat, HDAC inhibitors, cholecalciferol, calcitriol and combinations thereof.

Classifier Training—Inputs and Methods

Creation and optimization of the cell detection classifiers described above is generally referred to as "classifier training," as the process aims to accurately diagnose cells according to a reference or ground truth. Using the classification methods described herein, cells can be classified into types including, but not limited to, normal, cancerous, and dysplastic. There are two main aspects to accuracy: first is specificity (normal cells being called normal by the classifier), and second is sensitivity (abnormal cells being called abnormal by the classifier). Algorithm training methods include Adaptively Boosted Logistic Regression and Random Forest. Those skilled in the art will be familiar with how to apply other classical training techniques for classifiers such as template methods, adaptive processing and the like.

The methods used to train the classifier ensure an extremely good outcome given the data used as input. Primarily, classifier accuracy is ensured when the inputs to the classifier training process accurately describe clinically relevant aspects of the cells and are robust to environmental factors that could influence optical tomography system results:

1. As shown above with reference to FIG. 6A-FIG. 6D, three-dimensional cell images generated by the optical tomography system have high resolution, allowing precise measurements of critical features that support correct classification.
2. Some features that are useful in classification emerge only in the 3D image. Consequently, the 3D feature set is not only more descriptive of the cell but also richer making classification based on three-dimensional imaging more accurate versus 2D imaging.
3. Three-dimensional, image segmentation algorithms have been developed to isolate the whole cell from the background and the nucleus from the cell. The accuracy of these segmentation algorithms was verified by comparing the segmented trace with human derived cell or nuclear envelope traces.
4. Feature measurements describe various aspects of the cell, cell nucleus, cytoplasm and cell nucleoli. In one example of a test system, 594 features are computed for each 3D cell image that represent object shape, volume, distribution of chromatin, and other, subtler morphometric elements. Computation of these features has been verified to be independent of the orientation of the cell.
5. Diagnostic truth (the gold standard of pathology) for the classifier training is based on hierarchical cell diagnoses provided by two cytotechnologists and a cytopathologist.

Classifier Training—Statistical Considerations

Secondarily, in one test carried out by the inventors herein, accuracy of the classifier training process was ensured through a rigorous process that encompassed three aspects:

1. The database that was used to train the classifier was formulated to contain sufficient material to ensure that binomial 95% confidence intervals maintain variance of performance estimates within acceptable bounds.
2. Over-training is one potential pitfall of the training process where too much information could be included into the classifier so that the result could become over-specialized to the data used in the training. This situation generates an overly optimistic estimate for classifier performance. The risks of over-training can be mitigated through cross-validation which involves taking a portion of the training data and using it as testing data. Limits for the amount of information that can be used in the classifier are reached when performance estimates based on training data exceed the estimates from testing data
3. Finally, as further assurance against over-training, the classifier was tested on data from a second set of cells that were not a part of the training process.

Abnormal Cell Classifier Training Summary

The following considerations were used to define the parameters governing the training for the abnormal cell classifier 42:

1. Since abnormal cells in sputum samples are scarce, and non-diagnostic elements in sputum are plentiful the classifier must operate with high sensitivity and very high specificity. As described later in Table 1, high case detection sensitivity is maintained when the single cell classifier sensitivity is 75% and the specimen contains more than one abnormal cell.
2. To ensure workload is maintained within reasonable limits, the goal for specificity was set at 99%.
3. Intervals for the lower binomial 95% confidence bound (21) were to be maintained above 70% for sensitivity and 98.5% for specificity.

In the end, a high detection rate is desired for each positive case. Sensitivity of single cell detection translates to detection of the abnormal case as shown in Table 1.

TABLE 1

| Number of Abnormal Cells in the analysis | Case sensitivity based on 71% individual cell sensitivity (%) |
|---|---|
| 1 | 71.0 |
| 2 | 91.6 |
| 3 | 97.6 |

The implications of Table 1, are important for the lung cancer detection test. Results shown in this table indicate that if an abnormal cell is in the group analyzed by the lung cancer detection test, it will be confidently detected so that the case will be identified with high sensitivity. This leaves the question of abnormal cell presence in the lung cancer detection test analysis as the remaining factor determining the cancer detection rate.

Specimen Adequacy

Because sputum is a highly variable specimen from patient to patient, a process is needed to evaluate whether the cells analyzed by lung cancer detection test comprise sufficient lung sampling for disease detection. Classical sputum adequacy is assessed based on the presence of abundant alveolar macrophages, however, these cell types are not preserved through the lung cancer detection test cell enrichment process. Furthermore, prior evaluations of the relationship between macrophage presence and abnormal cell presence in sputum have not given confidence in this adequacy determination method. Consequently, the lung cancer detection test adequacy is based on an enumeration of reference cells, such as normal bronchial epithelial cells including metaplastic cells and columnar cells. The lung cancer detection test automatically enumerates these cells so that a separate manual analysis for adequacy is not required. As noted, lung cancer detection test specimen processing removes non-diagnostic elements in the sputum. This processing has the effect of randomizing the cellular content within the enriched cell pellet. This implies that the likelihood of encountering an abnormal cell during lung cancer detection test analysis of a specimen from a cancer patient depends primarily on the ratio of abnormal cells with the number of normal cells in the sample and the number of normal cells processed by lung cancer detection test. This ratio depends on many factors including the lesion size, dynamics of the cough, etc. Case detection then becomes primarily dependent on processing enough normal bronchial epithelial cells so that the abnormal cells are also processed.

Classifier Development and Features

Generally, features are computed to provide numerical representation of various aspects of the 3D tomogram. The computed features are used along with expert diagnosis of the objects to develop a classifier that can distinguish between object types. For example, a data set with M 3D tomograms computed for objects of a first type, type 1, and N 3D tomograms may be computed for objects of a second type, type 2, such as normal and abnormal cells. Here "M" and "N" represent the number of type 1 and type 2 values respectively. The data set is preferably generated by an optical tomography system. The optical tomography system provides 3D tomograms including 3D images of objects such as, for example, a cell. A cell typically includes other features such as a nucleus having organelles such as nucleoli. Object types may include differing types of cells, organelles, cells exhibiting selected disease states, probes, normal cells or other features of interest. A set of x 3D image features are computed based on 3D tomograms for all M+N objects. Next, a refined feature set of y 3D image features that best discriminate the object types is found, where "x" and "y" represent the number of 3D image features at each stage. The refined 3D image feature set of y 3D image features is used to build a classifier whose output correlates with the object type. In one example embodiment, at stage 102 a set of 3D tomograms is assembled, where the assembled set represent substantially all important markers that would be used by an expert to distinguish 3D biological object types. Having assembled a representative set of 3D tomograms, a 3D image feature set may be computed for each object that characterizes the important markers.

Features

Tomograms of biological objects, such as cells, exhibit a plurality of observable and measurable characteristics, some of which may be used as features for classification. Table 2 below provides a capsule summary of features, that is, important markers used to foster classification aims.

TABLE 2

FEATURES

| Feature Name | Brief Description |
|---|---|
| Volume | Number of connected voxels that comprise an object. |
| Surface Area | Number of voxels on the outer surface of a discrete object. |
| Shape features | Based on bounding box, surface area/volume ratio. |
| Location | Geometric center and center of mass of an object. |
| Voids | Based on a threshold T, number, volume, surface area, shape and location of inter-nuclear voids. |
| Invaginations | Based on a threshold T, count, size and location of nuclear invaginations. |
| Invagination Voids | Based on a threshold T, volume, surface area, shape, location of voids connected to invaginations. |
| Nucleoli | Based on a threshold T, volume, surface area, and shape, and location of objects likely to be nucleoli or chromatin condensations. |
| Nuclear texture features | The technique of a blur residue, using various sized structure elements, is used to separate various sized features within the nucleus. Overall 3D volume is then computed as are the number of discrete components, the volume histogram, average volume and variance, and shape histogram. |
| Distance metrics | Metrics describe spatial relationships between nucleoli, invaginations, voids, and the nuclear envelope. For example if three nucleoli are found the mean and variance, minimum and maximum inter-nucleoli distance may be found. Also the distance between the average coordinates for the cluster of the nucleoli and the center of mass for the entire object may be found. Similar calculations may be formed by substituting any of the above entities for the nucleoli and the nuclear center of mass. |
| FFT features | FFT of a 3D tomogram and FFT features characterize prominent and average FFT characteristics. |
| Histogram statistical features | Statistical features related to the 3D histogram of grey values for voxels such as kurtosis, the statistical moment of |
| 2D features | Two dimensional features include texture features such as blur residue and geometric features including perimeter and circularity of the object. |

By way of further explanation, in one useful example, voids occurring in 3D biological objects have now been found to be useful classification features based on measurement criteria including comparison with a calculated or selected threshold. Another characteristic related to voids may include the number of voids in an object. Another characteristic related to voids includes volume of a void or number of voids. Yet another characteristic includes surface area of a void or number of voids. Shape and location of inter-nuclear voids may also be employed as a useful feature characteristic. Additionally, combinations of feature characteristics may also be used to build a classifier as described hereinabove.

Similarly, invaginations occurring in 3D biological objects have now been found to be useful classification features based on measurement criteria including comparison with a calculated or selected threshold. Another characteristic related to invaginations may include the number of invaginations in an object. Another characteristic related to invaginations includes volume of an invaginations or number of invaginations. Yet another characteristic includes size of an invagination or number of invaginations. Location of nuclear invaginations also comprises a useful feature characteristic. Additionally, combinations of feature characteristics may also be used to build a classifier as described hereinabove.

Invaginations occurring in 3D biological objects have now been found to be useful classification features based on measurement criteria including comparison with a calculated or selected threshold. Volume of invagination voids, surface area, shape, location of voids connected to invaginations and combinations of invagination features may also be advantageously used to build a classifier as described hereinabove.

Nucleoli occurring in 3D biological objects have now been found to be useful classification features based on measurement criteria including comparison with a calculated or selected threshold. Volume, surface area, shape, location of objects likely to be nucleoli or chromatin condensations and combinations of the aforesaid characteristics may also be advantageously used to build a classifier as described hereinabove. Nuclear texture features occurring in 3D biological objects have now been found to be useful classification features. Using various sized structure elements, the technique of blur residue is used to separate various sized features within the nucleus. Blur residue techniques typically require blurring an image using a filter and measuring the resultant blur residue by applying marking operations. Overall 3D volume is then computed as are the number of discrete components, the volume histogram, average volume and variance, and shape histogram.

Distance metrics that describe spatial relationships between nucleoli, invaginations, voids, and the nuclear envelope have now been found to be useful classification features. For example, if three nucleoli are found the mean and variance, minimum and maximum inter-nucleoli distance may be found. Also, the distance between the average coordinates for the cluster of the nucleoli and the center of mass for the entire object may be found. Similar calculations may be formed by substituting any of the above entities for the nucleoli and the nuclear center of mass.

Fast Fourier Transform (FFT) features now have also been found to be useful classification features. FFT features are formed by a Fast Fourier Transform of a 3D tomogram. The FFT features characterize prominent and average characteristics of the FFT classification.

Example Methodologies

Having provided a detailed description of the methods and systems for determining dysplastic cells and treatment administration therefore, it is considered helpful to the understanding of the invention to provide some detailed examples of system construction and use.

In one example, a method for automated detection and monitoring of pre-cancerous cellular conditions by analyzing 3D images of cells based on pseudo-projections obtained from a sputum specimen obtained from a subject comprises operating a biological specimen classifier to identify cells from the sputum specimen as normal or abnormal. If abnormal cells are detected, then the abnormal cells are further classified as pre-cancerous or cancerous. If pre-cancerous cells are detected then a biological specimen classifier classifies cells from the sputum sample as: pre-cancerous cells of glandular origin, mild-moderate dysplasia, moderate to severe dysplasia or severe dysplasia. If the cells are classified as cancerous, then a biopsy is performed to verify suspicious lesions. If cancer is found, then surgical procedures remove the cancer lesion. If the cells are classified as pre-cancerous, then an immunomodulation agent and/or a cancer chemoprevention pharmaceutical is administered to the subject over a predetermined time period. If cells are classified as mild, moderate or severe dysplasia, then cancer chemoprevention pharmaceutical is administered to the subject over a predetermined time period. If both pre-cancerous and cancer cells are discovered then the cancer status of any suspicious lesions is verified and if cancer is found, then surgical procedures remove the cancer lesion, and a cancer chemoprevention pharmaceutical is administered to the subject over a predetermined time period.

In another example, the immunomodulating agent comprises a drug selected from the group consisting of a chimeric immunoreceptor, a prostacyclin analog, iloprost, a chimeric antigen receptor (CAR) for T-cells, Vorinostat, HDAC inhibitors, cholecalciferol, calcitriol and combinations thereof.

In another example, treatment calls for administering the an immunomodulation agent and/or a cancer chemoprevention pharmaceutical to the subject over a predetermined time period, then obtaining a second sputum specimen from the subject, and repeating the operation of the biological specimen classifier to classify cells as normal or abnormal. If abnormal cells are detected, then the abnormal cells are further classified as cancerous, precancerous cells of glandular origin, as mild to moderate dysplasia, moderate to severe dysplasia, severe dysplasia or cancerous; and the classification results of the repeated operation are compared with classification results from the previous operation to determine the effectiveness of the immunomodulation agent and/or a cancer chemoprevention pharmaceutical.

In another example, an optical tomography system for automated detection and monitoring of dysplasia by analyzing feature data from 3D images of cells obtained from a sputum specimen obtained from a subject includes a sample adequacy classifier coupled to receive the feature data and generate a sample adequacy value. A normal/abnormal cell classifier is coupled to receive the feature data and detect normal and abnormal cells. An abnormal cell classifier is coupled to the normal/abnormal cell classifier to receive data for the abnormal cells and further classify the abnormal cells into cancerous and pre-cancerous cells. A pre-cancerous cell classifier is coupled to the abnormal cell classifier to receive pre-cancerous cell data and identify each pre-cancerous cell as precancerous cells of glandular origin or dysplastic. A dysplastic cell classifier is coupled to pre-cancerous cell classifier to receive dysplastic cell data and further classify dysplastic cells as mild to moderate dysplasia, moderate to severe dysplasia, or severe dysplasia. A treatment protocol generator is adapted to receive classification data from the abnormal cell classifier, the pre-cancerous cell classifier, and the dysplastic cell classifier and responsively generate a protocol to administer an immunomodulation agent and/or a cancer chemoprevention pharmaceutical to the subject over a predetermined time period if indicated by the detection of cancer, pre-cancerous or dysplastic cells.

In another example, a method for automated detection and monitoring of dysplasia by analyzing 3D images of a cell obtained from a sputum sample obtained from a subject includes providing 3D imaging data for a cell contained in the sputum sample; providing a sample adequacy determination for the sputum sample; if the sample adequacy determination meets predetermined criteria, then operating a normal/abnormal classifier to generate a determination of normal/abnormal; if the determination is abnormal, then further identifying the cell as cancerous and then performing surgery to remove the tumor, pre-cancerous of glandular origin or dysplastic; if the cell is classified as cancerous, then determining whether the cell is squamous cancer or adenocarcinoma; and if the cell is dysplastic then administering an immunomodulation agent and/or a cancer chemoprevention pharmaceutical to the subject over a predetermined time period; if the determination is cancerous and dysplastic then performing surgery to remove the tumor and further administering a an immunomodulation agent and/or a cancer chemoprevention pharmaceutical to the subject over a predetermined time period.

In another example, a method for automated detection and monitoring of dysplasia by analyzing pseudo-projection images of cells obtained from a sputum sample includes providing 3D imaging data for a cell contained in the sputum sample. A sample adequacy determination is made for the sputum sample, and, if the sample adequacy determination meets predetermined criteria, then the cell data is identified as normal and metaplasia conditions, mild to moderate dysplasia or severe dysplasia or CIS and/or cancer. A subsequent optical tomography sputum test is scheduled within 12-24 months later if the cell data indicates a normal and metaplasia condition or within 6 months later if the cell data indicates mild to moderate dysplasia. A subsequent optical tomography sputum test is scheduled within 3 months later if the cell data indicates severe dysplasia and confirmation of the severe dysplasia is required followed by chemoprevention therapy. Follow-up diagnostic testing such as CT scans and bronchoscopy is scheduled within 6 months later severe dysplasia indicates CIS and/or cancer. An immunomodulation agent and/or a cancer chemoprevention pharmaceutical is administered to the subject over a predetermined time period if the cell is dysplastic.

In another example, a method of treating a malignancy in a human subject comprises analyzing 3D images of cells based on pseudo-projections obtained from a sputum specimen obtained from a subject; operating a biological specimen classifier to identify cells from the sputum specimen as normal or abnormal; further classifying identified abnormal cells as pre-cancerous or cancerous; further classifying pre-cancerous cells as pre-cancerous cells of glandular origin, mild-moderate dysplasia, moderate to severe dysplasia or severe dysplasia; when the cells are classified as cancerous, then performing a biopsy to verify suspicious lesions; when cancer is found, then administering surgical procedures to remove the cancer lesion; when the cells are classified as pre-cancerous of glandular origin, then conducting immunotherapy by administering an immunomodulating agent to a human subject over a predetermined time period to assist the immune system of the human subject in eradicating cancerous cells; when cells are classified as mild, moderate or severe dysplasia, then administering immunomodulating agent to the subject over a predetermined time period; and when both pre-cancerous and cancer cells are discovered, then verifying the cancer status of any suspicious lesions; when cancer is found, then administering surgical procedures to remove the cancer lesion, and administering an immunomodulating agent and/or chemotherapy to the subject over a predetermined time period.

In another example, the immunomodulating agent comprises a drug selected from the group consisting of a chimeric immunoreceptor, a prostacyclin analog, iloprost, a chimeric antigen receptor (CAR) for T-cells, Vorinostat, HDAC inhibitors, cholecalciferol, calcitriol and combinations thereof.

In another example, additional steps include obtaining a second sputum specimen from the subject; repeating operation of the biological specimen classifier to classify cells as normal or abnormal; when abnormal cells are detected, then further classifying the abnormal cells cancerous, precancerous cells of glandular origin, as mild to moderate dysplasia, moderate to severe dysplasia, severe dysplasia or cancerous; and comparing the classification results of the repeated operation with classification results from the previous operation to determine the effectiveness of the immunomodulating agent.

In another example, a subsequent optical tomography sputum test is scheduled within 12-24 months later if the cell data indicates a normal and metaplasia condition.

In another example, a subsequent optical tomography sputum test is scheduled within 6 months later if the cell data indicates mild to moderate dysplasia.

In yet another example, a subsequent optical tomography sputum test is scheduled within 3 months later if the cell data indicates severe dysplasia.

In yet another example, a subsequent optical tomography sputum test is scheduled within 3 months later if the cell data indicates pre-cancerous conditions of glandular origin.

In another example, confirmation of the severe dysplasia is required followed by immunomodulation therapy.

In another example, follow-up diagnostic testing such as CT scans and bronchoscopy is scheduled within 6 months later severe dysplasia indicates CIS and/or cancer.

In another example, an immunomodulation agent is administered to the subject over a predetermined time period if the cell is dysplastic.

In yet another example, a method for automated detection and monitoring of dysplasia by analyzing 3D images of cells obtained from a sputum sample includes providing 3D imaging data for a cell contained in the sputum sample; providing a sample adequacy determination for the sputum sample; if the sample adequacy determination meets predetermined criteria, then identifying the cell data as normal and metaplasia conditions, pre-cancerous cells of glandular origin, mild to moderate dysplasia or severe dysplasia or CIS and/or cancer.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A method of training and using an automated dysplastic cell algorithmic classifier directed to treating a malignancy in a subject comprising:

a) obtaining a set of known unique dysplastic cells indicating an abnormal lung process and a plurality of known normal cells;
b) operating an optical tomography system to generate a first set of 3D images of the set of known unique dysplastic cells indicating an abnormal lung process and a second set of 3D images for the plurality of known normal cells;
c) computing a plurality of dysplastic cell feature measurements from the first set of 3D images;
d) computing a plurality of normal cell feature measurements from the second set of 3D images;
e) operating a training algorithm using the plurality of dysplastic cell feature measurements and the normal cell feature measurements to classify the set of known unique dysplastic cells and plurality of known normal cells into classified dysplastic cell types and classified normal cell types;
f) comparing the classified dysplastic cell types and classified normal cell types with diagnostic truth to determine an accuracy value;
g) comparing the accuracy value to a predetermined performance bound;
h) if the accuracy value does not fall within the predetermined performance bound, then adjusting dysplastic cell feature values for each of the plurality of dysplastic cell feature measurements and adjusting normal cell feature values for each of the plurality of normal cell feature measurements according to the training algorithm;
i) repeating steps e) through h) until the accuracy value falls within the predetermined performance bound and providing the last adjusted dysplastic cell feature values for each of the plurality of dysplastic cell feature measurements as trained dysplastic cell feature measurements and providing the last adjusted normal cell feature values for each of the plurality of normal cell feature measurements as trained normal cell feature measurements;
j) inputting the trained dysplastic cell feature measurements and trained normal cell feature measurements into a dysplastic classifier;
k) operating the optical tomography system to generate a third set of 3D patient images of cells based on pseudo-projections obtained from a patient specimen derived from spontaneous cough sputum;
l) operating the dysplastic cell classifier to determine whether cells represented by the third set of 3D patient images comprise dysplastic cell types; and
m) when cells represented by the third set of 3D patient images are classified as dysplastic cell types, then administering an immunomodulating agent to the subject over a predetermined time period.

2. The method of claim 1 wherein the training algorithm is selected from the group consisting of Adaptively Boosted Logistic Regression, Random Forest and combinations thereof.

3. The method of claim 1 wherein the plurality of dysplastic cell feature measurements is selected from the group consisting of volume, surface area, shape features, invaginations, nuclear texture features, distance metrics, FFT features, histogram statistical features, 2D features and combinations thereof.

4. The method of claim 1 wherein the immunomodulating agent comprises a drug selected from the group consisting of a chimeric immunoreceptor, a prostacyclin analog, iloprost, a chimeric antigen receptor (CAR) for T-cells, Vorinostat, HDAC inhibitors, cholecalciferol, calcitriol and combinations thereof.

* * * * *